US006780974B2

(12) United States Patent
Chen et al.

(10) Patent No.: US 6,780,974 B2
(45) Date of Patent: Aug. 24, 2004

(54) SYNTHETIC DNA ENCODING AN ORANGE SEAPEN-DERIVED GREEN FLUORESCENT PROTEIN WITH CODON PREFERENCE OF MAMMALIAN EXPRESSION SYSTEMS AND BIOSENSORS

(75) Inventors: Yih-Tai Chen, Gibsonia, PA (US); Longguang Cao, Boulder, CO (US)

(73) Assignee: Cellomics, Inc., Pittsburgh, PA (US)

( * ) Notice: Subject to any disclaimer, the term of this patent is extended or adjusted under 35 U.S.C. 154(b) by 291 days.

(21) Appl. No.: 09/977,897

(22) Filed: Oct. 15, 2001

(65) Prior Publication Data

US 2002/0197673 A1 Dec. 26, 2002

Related U.S. Application Data

(60) Provisional application No. 60/297,645, filed on Jun. 12, 2001.

(51) Int. Cl.$^7$ ................................................ C07K 1/00
(52) U.S. Cl. .................................................... 530/350
(58) Field of Search ....................... 530/350; 536/23.1; 435/69.1

(56) References Cited

U.S. PATENT DOCUMENTS

| | | |
|---|---|---|
| 5,401,629 A | 3/1995 | Harpold et al. |
| 5,436,128 A | 7/1995 | Harpold et al. |
| 5,491,084 A | 2/1996 | Chalfie et al. |
| 5,786,464 A | 7/1998 | Seed |
| 5,795,737 A | 8/1998 | Seed et al. |
| 5,874,304 A | 2/1999 | Zolotukhin et al. |
| 5,968,750 A | 10/1999 | Zolotukhin et al. |
| 6,232,107 B1 | 5/2001 | Bryan et al. |

OTHER PUBLICATIONS

Journal of Virology,Jul., 1996, p. 4646–4654, vol. 70, No. 7, "A "Humanized" Green Fluorescent . . . Mammalian Cells", S.Zolotukhin, et al.
Current Biology 1996, vol. 6, No. 3:325–330, "Engineered GFP as a Vital Reporter in Plants", Wan–ling Chiu, et al.
European Journal of Cell Biology, vol. 79, pp. 144–149(Feb. 2000) "Expression of the Green . . . tetraurelia", Karin Hauser, et al.
Journal of Protein Chemistry, vol. 20,No. 6, Aug. 2001, p. 507–519 "Characterization and Use of Green Fluorescent Proteins . . . Functional Peptides", Beau Peelle, et al.
Barber, K., et al., Delivery of membrane–impermeant fluorescent probes into living neural cell populations by lipotransfer, Neuroscience Letters 207 (1996) 17–20, Elsevier Science Ireland Ltd. Publ.
Brejc, K., et al., Structural basis for dual excitation and photoisomerization of the Aequorea victoria green fluorescent protein, Proc. Natl. Acad. Sci. USA vol. 94, pp. 2306–2311, Mar. 1997 Biophysics, The National Academy of Sciences of the USA Publ.

Bright, G., et al., Delivery of Macromolecules into Adherent Cells via Electroporation for Use in Fluorescence Spectroscopic Imaging and Metabolic Studies, Cytometry 24:226–233 (1996), Wiley–Liss, Inc. Publ.
Barak, L., et al., A B–Arrestin/Green Fluorescent Protein Biosensor for Detecting G Protein–coupled Receptor Activation, The Journal of Biological Chemistry, vol. 272 No. 44, Issue of Oct. 31, pp 27497–27500 (1997), The American Society for Biochemistry and Molecular Biology, Inc. Publ.
Chalfie, M., et al., Green Fluorescent Protein as a Marker for Gene Expression, Science vol. 263, pp. 802–805, Feb. 11, 1994.
Cheng, L. et al., Use of green fluorescent protein variants to monitor gene transfer and expression in mammalian cells, Research Division SyStemix, Inc. Palo Alto, CA 94304, ' Oncology Ressearch Laboratories, The Toronto Hospital and Department of Medical Biophysics, Univeristy of Toronto, Toronto, Ontario M5G2M1, Canada, Feb. 23, 1996.
Cubitt, A. et al., Understanding, improving and using green fluorescent proteins, TIBS 20—Nov. 1995, pp. 448–455, Elsevier Science Ltd.
Davis, I., et al., A Nuclear GFP That Marks Nuclei in Living Drosophila Embryos; Maternal Supply Overcomes a Delay in Appearance of Zygotic Fluorescence, Developmental Biology 170, 726–729 (1995), Academic Press, Inc. Publ.
Ehrig, T., et al., Green–fluorescent protein mutants with altered fluorescence excitation spectra, FEBS Leters 367 (1995) 163–166, Federation of European Biochemical Societies Publ.
Giuliano, K.; et al., Fluorescent Protein Biosensors: Measurement of Molecular Dynamics in Living Cells, Annu. Rev. Biophys. Biomol. Struct. (1995) 24:405–34, Annual Reviews Inc. Publ.
Giuliano, K.A, and Taylor, D. L., Light–Optical–Based Reagents for the Measurement and Manipulation of Ions, Metabolites, and Macromolecules in Living Cells, Methods in Neurosciences, vol. 27, pp. 1–16 (1995), Academic Press Inc., Publ., San Diego, California, USA.
Haas, J., Codon usage limitation in the expression of HIV–1 envelope glycoprotein, Current Biology (1996), vol. 6 No. 3:315–324, Current Biology Ltd. Publ.

(List continued on next page.)

Primary Examiner—Karen Cochrane Carlson
Assistant Examiner—Sheridan K Snedden
(74) Attorney, Agent, or Firm—Craig G. Cochenour; Jose J. Aparicio; Buchanan Ingersoll PC

(57) ABSTRACT

Synthetic versions of a full length and termini truncated humanized green fluorescent protein based on *Ptilosarcus gurneyi* are disclosed which have been modified to the favored or most favored codons for mammalian expression systems. The disclosed encoded protein has 239 amino acid residues compared with the wild type *Ptilosarcus gurneyi* which has 238 amino acids. In the present invention, a valine residue has been added at the second position from the amino terminus and codon preference bias has been changed in a majority of the wild type codons of *Ptilosarcus gurneyi* fluorescent protein. The humanized *Ptilosarcus gurneyi* green fluorescent protein is useful as a fluorescent tag for monitoring the activities of its fusion partners using imaging based approaches.

4 Claims, 20 Drawing Sheets

OTHER PUBLICATIONS

Haseloff, J., et al., Removal of a cryptic intron and subcellular localization of green fluorescent protein are required to mark transgenic Arabidopsis plants brightly, Proc. Natl. Acad. Sci. USA vol. 94, pp 2122–2127, Mar. 1997 Applied Biological Sciences, The National Academy of Sciences of the USA Publ.

Hastings, W. Bioluminescence, Chapter 48 in Cell Physiology Source Book, Ed. By Nicholas Sperelakis, pp. 665–681, (1995) Academic Press, Inc. Publ., San Diego, California, USA.

Heim, R., et al., Engineering green fluorescent protein for improved brightness, longer wavelengths and fluorescence resonance energy transfer, Current Biology 1996, 6:178–182, Current Biology Ltd., Publ.

Jones, J. et al., Development and Application of a GFP–FRET intracellular Caspase Assay for Drug Screening., Journal of Biomolecular Screening, vol. 5, No. 5, pp. 307–318 (2000), The Society for Biomolecular Screening Publ., San Diego, California, USA.

McNeil, P., Incorporation of Macromolecules into Living Cells, Methods in Cell Biology, vol. 29, pp. 153–173 (1989) Academic Press, Inc. Publ.

Miyawaki, A., et al., Fluorescent indicators for $Ca^{2+}$ based on green fluorescent proteins and calmodulin, Nature, vol. 388, pp. 882–887, Aug. 28, 1997, Macmillan Publishers Ltd. (1997) Publ.

Morise, H. et al, Intermolecular Energy Tranfser in the Bioluminescent System of Aequorea, Biochemistry, vol. 13, No. 12, pp. 2656–2662 (1974).

Rizzuto, R., et al., Rapid changes of mitochondrial $Ca^2$ revealed by specifically targeted recombinant aequorin, Nature, vol. 358, pp. 325–327, Jul. 23, 1992.

Kaether, C. et al., Visualization of protein transport along the secretory pathway using green fluorescent protein, FEBS Letters 369 (1995) 267–271, Federation of European Biochemical Societies Publ.

Hu, W., et al., Expression of Aequorea green fluorescent protein in plant cells, FEBS Letters 369 (1995) 331–334, Federation of European Biochemical Societies Publ.

Southwick, P., et al., Cyanine Dye Labeling Reagents–Carboxymethylindocyanine Succinimidyl Esters, Cytometry 11:418–430 (1990), Wiley–Lisa, Inc. Publ.

Tsien, R., Fluorescent Indicators of Ion Concentrations, Methods In Cell Biology, Ch. 5, pp. 127–156 (1989), Academic Press, Inc. Publ.

Wang, Y., et al., Fluorescent Analog Cytochemistry: Tracing Functional Protein Components in Living Cells, Methods in Cell Biology, vol. 29, pp. 1–12 (1989) Academic Press, Inc. Publ.

Ward, W., et al., Reversible Denaturation of Acquorea Green–Fluorescent Protein: Physical Separation and Charaterization of the Renatured Protein, Biochemistry 1982, 21, 4535–4540, (1982) American Chemical Society Publ.

Ward, W., et al., Spectrophotometric Identity of the Energy Transer Chromophores in Renilla and Aequorea Green–Fluorescent Proteins, Photochemistry and Photobiology, vol. 31, pp 611 to 615, (1980) Pergamon Press Ltd Publ.

Ward, W., Ch. 7: General Aspects of Bioluminescence, Chemi– and Bioluminescence, pp. 321–358, Edited by John G. Burr, (1985) Marcel Dekker, Publ., New York, New York.

Waud, J., et al., Measurement of proteases using chemiluminescence–resonance–energy–transfer chimaeras between green fluorescent protein and aequorin, Biochem J. (2001) 357, 687–697 Biochemical Society Publ.

Johnson, F.H., Luminescence, Narcosis, and Life In The Deep Sea, Vantage Press, 1st Ed., pp. 50–57 (1988).

Figure 1
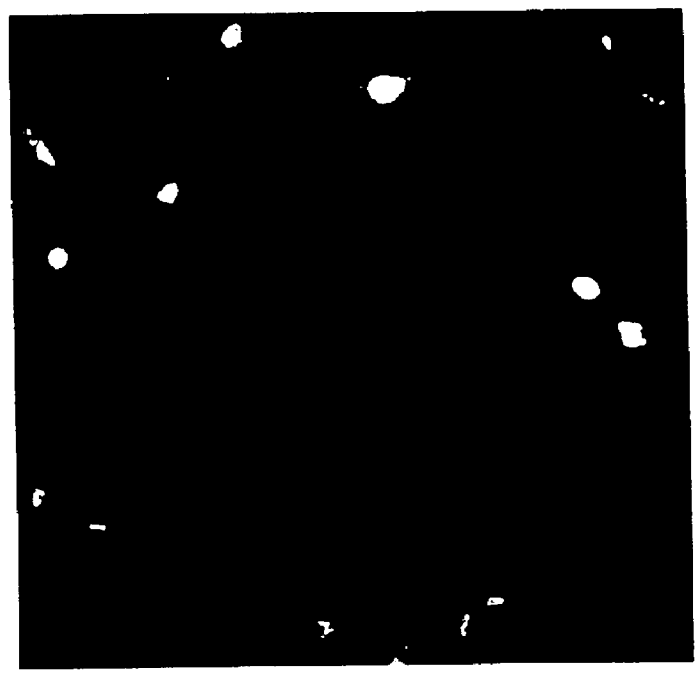
Green Fluorescent Protein
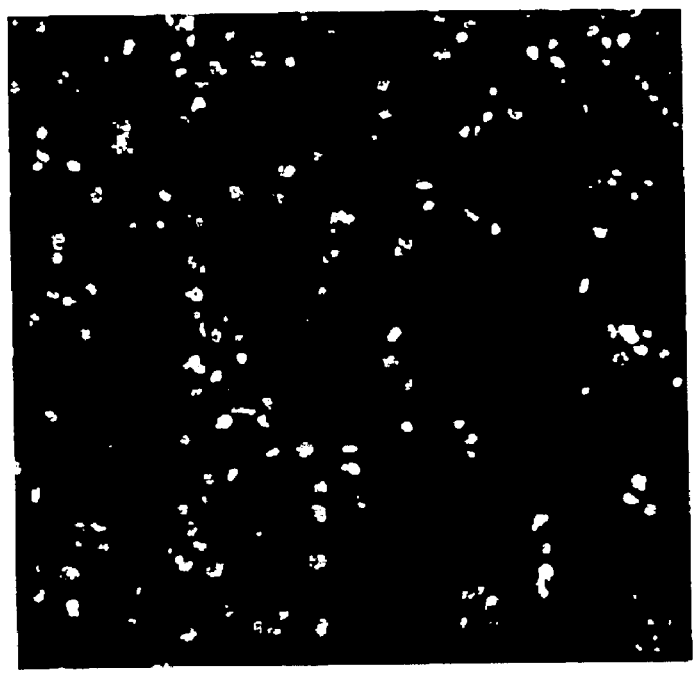
Hoechst 33342 Stain

Figure 4

Figure 6
A
B
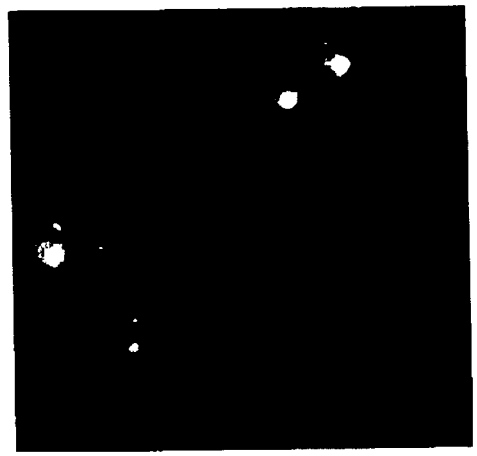
C
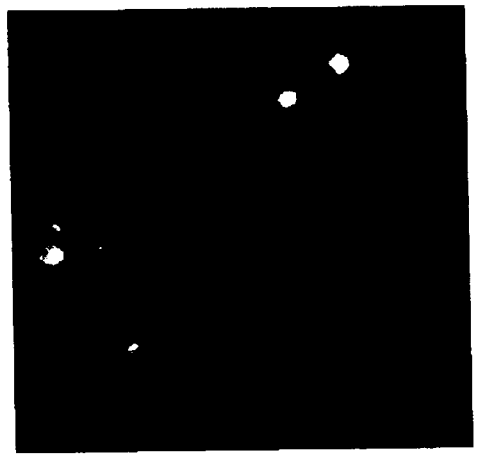

Figure 9

```
                    Met
                Met Val
          +1        Asn Arg Asn Val Leu Lys Asn Thr Gly Leu Lys Glu Ile Met Ser Ala Lys Ala
PtFP    1         ATG AAC CGC AAC GTA TTA AAG AAC ACT GGA CTG AAA GAG ATT ATG TCG GCA AAA GCT
hPtFP   1     ATG GTG AAC CGG AAC GTG CTG AAG AAC ACC GGC CTG AAG GAG ATC ATG AGC GCC AAG GCC
              ***     *    *  *        *      *    *     *     *    *   *** *    *    *

+1 Ser Val Glu Gly Ile Val Asn Asn His Val Phe Ser Met Glu Gly Phe Gly Lys Gly Asn
PtFP    61   AGC GTT GAA GGA ATC GTG AAC AAT CAC GTT TTT TCC ATG GAA GGA TTT GGA AAA GGC AAT
hPtFP   61   AGC GTG GAG GGC ATC GTG AAC AAC CAC GTG TTC AGC ATG GAG GGC TTC GGC AAG GGC AAC
                 *   *   *           *       *   *   *   *  **       *     *   *   *   *

+1 Val Leu Phe Gly Asn Gln Leu Met Gln Ile Arg Val Thr Lys Gly Gly Pro Leu Pro Phe
PtFP   121   GTA TTA TTT GGA AAC CAA TTG ATG CAA ATC CGG GTT ACA AAG GGA GGT CCG TTG CCA TTC
hPtFP  121   GTG CTG TTC GGC AAC CAG CTG ATG CAG ATC CGG GTG ACC AAG GGC GGC CCT CTG CCC TTC
             *   *   *   *       *   *       *           *   *   *   *   *   *   *   *

+1 Ala Phe Asp Ile Val Ser Ile Ala Phe Gln Tyr Gly Asn Arg Thr Phe Thr Lys Tyr Pro
PtFP   181   GCT TTC GAT ATT GTT TCC ATA GCT TTC CAA TAC GGG AAT CGC ACT TTC ACG AAA TAC CCA
hPtFP  181   GCC TTC GAC ATC GTG AGC ATC GCC TTC CAG TAC GGC AAC CGG ACC TTC ACC AAG TAT CCC
             *       *   *   *   *   **  *       *       *   *   *   *       *   *   *   *

+1 Asp Asp Ile Ala Asp Tyr Phe Val Gln Ser Phe Pro Ala Gly Phe Phe Tyr Glu Arg Asn
PtFP   241   GAC GAC ATT GCG GAC TAC TTT GTT CAA TCA TTC CCG GCT GGA TTT TTC TAC GAA AGA AAT
hPtFP  241   GAC GAC ATC GCC GAC TAC TTC GTG CAG AGC TTC CCT GCC GGC TTC TTC TAC GAG CGG AAC
                     *   *       *   *   *   *   ***     *   *   *   *           *   *** *

+1 Leu Arg Phe Glu Asp Gly Ala Ile Val Asp Ile Arg Ser Asp Ile Ser Leu Glu Asp Asp
PtFP   301   CTA CGC TTT GAA GAT GGC GCC ATT GTT GAC ATT CGT TCA GAT ATA AGT TTA GAA GAT GAT
hPtFP  301   CTG CGG TTC GAG GAC GGC GCC ATC GTG GAC ATC CGG AGC GAC ATC AGC CTG GAG GAC GAC
             *    *  *   *   *           *   *       *   *   *   *   *** *   *   *** *   *

+1 Lys Phe His Tyr Lys Val Glu Tyr Arg Gly Asn Gly Phe Pro Ser Asn Gly Pro Val Met
PtFP   361   AAG TTC CAC TAC AAA GTG GAG TAT AGA GGC AAC GGT TTC CCT AGT AAC GGA CCC GTG ATG
hPtFP  361   AAG TTC CAC TAC AAG GTG GAG TAC CGC GGC AAC GGC TTC CCT AGC AAC GGC CCT GTG ATG
                             *           *   *** *       *           *       *   *

+1 Gln Lys Ala Ile Leu Gly Met Glu Pro Ser Phe Glu Val Val Tyr Met Asn Ser Gly Val
PtFP   421   CAA AAA GCC ATC CTC GGC ATG GAG CCA TCG TTT GAG GTG GTC TAC ATG AAC AGC GGC GTT
hPtFP  421   CAG AAG GCC ATC CTG GGC ATG GAG CCC AGC TTC GAG GTG GTG TAC ATG AAC AGC GGC GTG
             *   *           *           *   * *** *                   *                   *

+1 Leu Val Gly Glu Val Asp Leu Val Tyr Lys Leu Glu Ser Gly Asn Tyr Tyr Ser Cys His
PtFP   481   CTG GTG GGC GAA GTA GAT CTC GTT TAC AAA CTC GAG TCA GGG AAC TAT TAC TCG TGC CAC
hPtFP  481   CTG GTG GGC GAG GTG GAC CTG GTG TAC AAG CTG GAG AGC GGC AAC TAC TAC AGC TGC CAC
                         *   *   *   *   *       *   *       *   *       *   *   ***     ***

+1 Met Lys Thr Phe Tyr Arg Ser Lys Gly Gly Val Lys Glu Phe Pro Glu Tyr His Phe Ile
PtFP   541   ATG AAA ACG TTT TAC AGA TCC AAA GGT GGA GTG AAA GAA TTC CCG GAA TAT CAC TTT ATC
hPtFP  541   ATG AAG ACC TTC TAC CGG AGC AAG GGC GGC GTG AAG GAG TTC CCT GAG TAC CAC TTC ATC
                 *   *   *   *   **   *   *   *       *   *       *   *   *   *       *

+1 His His Arg Leu Glu Lys Thr Tyr Val Glu Glu Gly Ser Phe Val Glu Gln His Glu Thr
PtFP   601   CAT CAT CGT CTG GAG AAA ACC TAC GTG GAA GAA GGA AGC TTC GTG GAA CAA CAC GAG ACG
hPtFP  601   CAC CAC CGG CTG GAG AAG ACC TAC GTG GAG GAG GGC AGC TTC GTG GAG CAG CAC GAG ACC
             *   *   *           *               *   *   *                 *   *       *

+1 Ala Ile Ala Gln Leu Thr Thr Ile Gly Lys Pro Leu Gly Ser Leu His Glu Trp Val ***.
PtFP   661   GCC ATT GCA CAA CTG ACC ACA ATT GGA AAA CCT CTG GGC TCC CTT CAT GAA TGG GTG TAG
hPtFP  661   GCC ATC GCC CAG CTG ACC ACC ATC GGC AAG CCT CTG GGC AGC CTG CAC GAG TGG GTG TAA
                 *   *   *           *   *   *   *           *       ** *   *           *
```

Figure 10

```
    HindIII
    -------
+1                M   V   N   R   N   V   L   K   N   T   G
  1   AAG CTT GCC ACC ATG GTG AAC CGG AAC GTG CTG AAG AAC ACC GGC
      TTC GAA CGG TGG TAC CAC TTG GCC TTG CAC GAC TTC TTG TGG CCG +1    L   K   E   I   M   S   A   K   A   S   V   E   G   I   V
 46   CTG AAG GAG ATC ATG AGC GCC AAG GCC AGC GTG GAG GGC ATC GTG
      GAC TTC CTC TAG TAC TCG CGG TTC CGG TCG CAC CTC CCG TAG CAC +1    N   N   H   V   F   S   M   E   G   F   G   K   G   N   V
 91   AAC AAC CAC GTG TTC AGC ATG GAG GGC TTC GGC AAG GGC AAC GTG
      TTG TTG GTG CAC AAG TCG TAC CTC CCG AAG CCG TTC CCG TTG CAC +1    L   F   G   N   Q   L   M   Q   I   R   V   T   K   G   G
136   CTG TTC GGC AAC CAG CTG ATG CAG ATC CGG GTG ACC AAG GGC GGC
      GAC AAG CCG TTG GTC GAC TAC GTC TAG GCC CAC TGG TTC CCG CCG +1    P   L   P   F   A   F   D   I   V   S   I   A   F   Q   Y
181   CCT CTG CCC TTC GCC TTC GAC ATC GTG AGC ATC GCC TTC CAG TAC
      GGA GAC GGG AAG CGG AAG CTG TAG CAC TCG TAG CGG AAG GTC ATG +1    G   N   R   T   F   T   K   Y   P   D   D   I   A   D   Y
226   GGC AAC CGG ACC TTC ACC AAG TAT CCC GAC GAC ATC GCC GAC TAC
      CCG TTG GCC TGG AAG TGG TTC ATA GGG CTG CTG TAG CGG CTG ATG +1    F   V   Q   S   F   P   A   G   F   F   Y   E   R   N   L
271   TTC GTG CAG AGC TTC CCT GCC GGC TTC TTC TAC GAG CGG AAC CTG
      AAG CAC GTC TCG AAG GGA CGG CCG AAG AAG ATG CTC GCC TTG GAC +1    R   F   E   D   G   A   I   V   D   I   R   S   D   I   S
316   CGG TTC GAG GAC GGC GCC ATC GTG GAC ATC CGG AGC GAC ATC AGC
      GCC AAG CTC CTG CCG CGG TAG CAC CTG TAG GCC TCG CTG TAG TCG +1    L   E   D   D   K   F   H   Y   K   V   E   Y   R   G   N
361   CTG GAG GAC GAC AAG TTC CAC TAC AAG GTG GAG TAC CGC GGC AAC
      GAC CTC CTG CTG TTC AAG GTG ATG TTC CAC CTC ATG GCG CCG TTG +1    G   F   P   S   N   G   P   V   M   Q   K   A   I   L   G
406   GGC TTC CCT AGC AAC GGC CCT GTG ATG CAG AAG GCC ATC CTG GGC
      CCG AAG GGA TCG TTG CCG GGA CAC TAC GTC TTC CGG TAG GAC CCG +1    M   E   P   S   F   E   V   V   Y   M   N   S   G   V   L
451   ATG GAG CCC AGC TTC GAG GTG GTG TAC ATG AAC AGC GGC GTG CTG
      TAC CTC GGG TCG AAG CTC CAC CAC ATG TAC TTG TCG CCG CAC GAC +1    V   G   E   V   D   L   V   Y   K   L   E   S   G   N   Y
496   GTG GGC GAG GTG GAC CTG GTG TAC AAG CTG GAG AGC GGC AAC TAC
      CAC CCG CTC CAC CTG GAC CAC ATG TTC GAC CTC TCG CCG TTG ATG

```
541 TAC AGC TGC CAC ATG AAG ACC TTC TAC CGG AGC AAG GGC GGC GTG
    ATG TCG ACG GTG TAC TTC TGG AAG ATG GCC TCG TTC CCG CCG CAC

+1   K   E   F   P   E   Y   H   F   I   H   H   R   L   E   K
586 AAG GAG TTC CCT GAG TAC CAC TTC ATC CAC CAC CGG CTG GAG AAG
    TTC CTC AAG GGA CTC ATG GTG AAG TAG GTG GTG GCC GAC CTC TTC

+1   T   Y   V   E   E   G   S   F   V   E   Q   H   E   T   A
631 ACC TAC GTG GAG GAG GGC AGC TTC GTG GAG CAG CAC GAG ACC GCC
    TGG ATG CAC CTC CTC CCG TCG AAG CAC CTC GTC GTG CTC TGG CGG

+1   I   A   Q   L   T   T   I   G   K   P   L   G   S   L   H
676 ATC GCC CAG CTG ACC ACC ATC GGC AAG CCT CTG GGC AGC CTG CAC
    TAG CGG GTC GAC TGG TGG TAG CCG TTC GGA GAC CCG TCG GAC GTG

Not I
                                         -----------
    +1   E   W   V   *
721 GAG TGG GTG TAA AGC GGC CGC
    CTC ACC CAC ATT TCG CCG GCG
```

The coding sequence (from start codon to stop codon):
atggtgaaccggaacgtgctgaagaacaccggcctgaaggagatcatgagcgccaag
gccagcgtggagggcatcgtgaacaaccacgtgttcagcatggagggcttcggcaag
ggcaacgtgctgttcggcaaccagctgatgcagatccgggtgaccaagggcggccct
ctgcccttcgccttcgacatcgtgagcatcgccttccagtacggcaaccggaccttc
accaagtatcccgacgacatcgccgactacttcgtgcagagcttccctgccggcttc
ttctacgagcggaacctgcggttcgaggacggcgccatcgtggacatccggagcgac
atcagcctggaggacgacaagttccactacaaggtggagtaccgcggcaacggcttc
cctagcaacggccctgtgatgcagaaggccatcctgggcatggagcccagcttcgag
gtggtgtacatgaacagcggcgtgctggtgggcgaggtggacctggtgtacaagctg
gagagcggcaactactacagctgccacatgaagaccttctaccggagcaagggcggc
gtgaaggagttccctgagtaccacttcatccaccaccggctggagaagacctacgtg
gaggagggcagcttcgtggagcagcacgagaccgccatcgcccagctgaccaccatc
ggcaagcctctgggcagcctgcacgagtgggtgtaa

Figure 11

```
aagcttgccaccatggtgaaccggaacgtgctgaagaacaccggcctgaaggagatc
atgagcgccaaggccagcgtggagggcatcgtgaacaaccacgtgttcagcatggag
ggcttcggcaagggcaacgtgctgttcggcaaccagctgatgcagatccgggtgacc
aagggcggccctctgcccttcgccttcgacatcgtgagcatcgccttccagtacggc
aaccggaccttcaccaagtatcccgacgacatcgccgactacttcgtgcagagcttc
cctgccggcttcttctacgagcggaacctgcggttcgaggacggcgccatcgtggac
atccggagcgacatcagcctggaggacgacaagttccactacaaggtggagtaccgc
ggcaacggcttccctagcaacggccctgtgatgcagaaggccatcctgggcatggag
cccagcttcgaggtggtgtacatgaacagcggcgtgctggtgggcgaggtggacctg
gtgtacaagctggagagcggcaactacacagctgccacatgaagaccttctaccgg
agcaagggcggcgtgaaggagttccctgagtaccacttcatccaccaccggctggag
aagacctacgtggaggagggcagcttcgtggagcagcacgagaccgccatcgcccag
ctgaccaccatcggcaagcctctgggcagcctgcacgagtgggtgtaaagcggccgc
```

| | Fluorescent? | Sequence |
|---|---|---|
| hPtFP | +++++++ | MV NRNVLKNT GLK □ EIMSA [____] QLT TIG KPLGSLHEWV |
| TS1 | + | MV LKNT GLK □ EIMSA [____] QLT TIG KPLGSLHEWV |
| TS2 | + | MV NT GLK □ EIMSA [____] QLT TIG KPLGSLHEWV |
| TS3 | + | MV GLK □ EIMSA [____] QLT TIG KPLGSLHEWV |
| TS4 | − | MV K □ EIMSA [____] QLT TIG KPLGSLHEWV |
| TS5 | + | MV NRNVLKNT GLK □ EIMSA [____] QLT TIG KPLGSL |
| TS6 | ++ | MV NRNVLKNT GLK □ EIMSA [____] QLT TIG KPL |
| TS7 | + | MV NRNVLKNT GLK □ EIMSA [____] QLT TIG |
| TS8 | + | MV NRNVLKNT GLK □ EIMSA [____] QLT |
| TS9 | + | MV NRNVLKNT GLK □ EIMSA [____] Q |
| TS10 | − | MV GLK □ EIMSA [____] QLT |
| TS11 | − | MV K □ EIMSA [____] Q |

Positions: 10, 224, 230, 239

Figure 14
no treatment
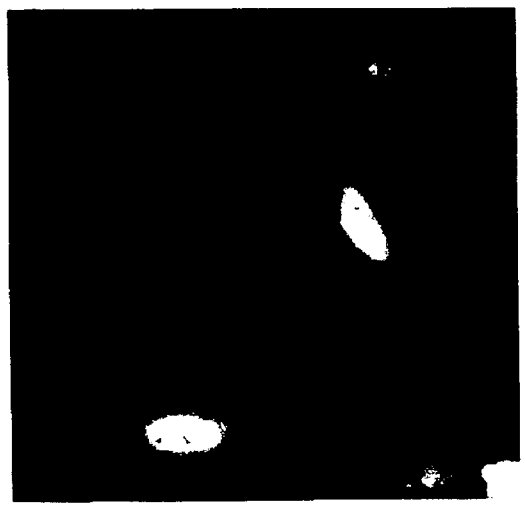
Staurosporine
10 nM 6 hours
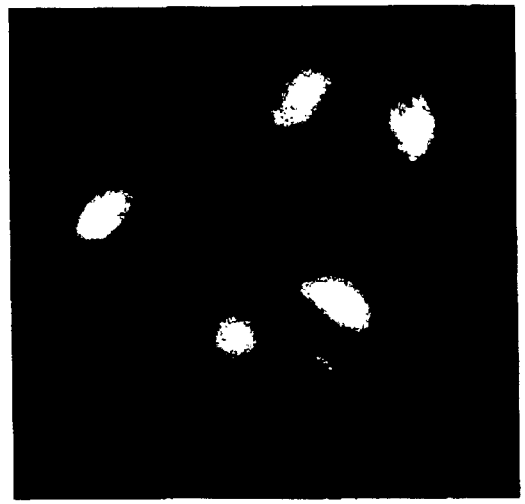
Staurosporine
1 nM 24 hours

| | | | | | | | | | | | |
|---|---|---|---|---|---|---|---|---|---|---|---|
| UUU | F | 0.45 | (185619) | UCU | S | 0.18 | (161556) | UAU | Y | 0.43 | (133427) | UGU | C | 0.45 | (108740) |
| UUC | F | 0.55 | (225633) | UCC | S | 0.22 | (192616) | UAC | Y | 0.57 | (174805) | UGC | C | 0.55 | (134523) |
| UUA | L | 0.07 | ( 79303) | UCA | S | 0.15 | (128429) | UAA | * | 0.29 | ( 8187) | UGA | * | 0.50 | ( 14381) |
| UUG | L | 0.13 | (135218) | UCG | S | 0.06 | ( 49456) | UAG | * | 0.21 | ( 5913) | UGG | W | 1.00 | (142435) |
| CUU | L | 0.13 | (139009) | CCU | P | 0.28 | (189374) | CAU | H | 0.41 | (113684) | CGU | R | 0.08 | (131222) |
| CUC | L | 0.20 | (210903) | CCC | P | 0.33 | (219428) | CAC | H | 0.59 | (162826) | CGC | R | 0.19 | (211962) |
| CUA | L | 0.07 | ( 75667) | CCA | P | 0.27 | (182506) | CAA | Q | 0.26 | (130857) | CGA | R | 0.11 | ( 68664) |
| CUG | L | 0.40 | (435317) | CCG | P | 0.11 | ( 76684) | CAG | Q | 0.74 | (377006) | CGG | R | 0.21 | (126679) |
| AUU | I | 0.35 | (174021) | ACU | T | 0.24 | (140780) | AAU | N | 0.46 | (186915) | AGU | S | 0.15 | (131222) |
| AUC | I | 0.49 | (240138) | ACC | T | 0.36 | (213626) | AAC | N | 0.54 | (218376) | AGC | S | 0.24 | (211962) |
| AUA | I | 0.16 | ( 78463) | ACA | T | 0.28 | (162837) | AAA | K | 0.42 | (262630) | AGA | R | 0.20 | (125600) |
| AUG | M | 1.00 | (244236) | ACG | T | 0.12 | ( 69346) | AAG | K | 0.58 | (359627) | AGG | R | 0.20 | (123646) |
| GUU | V | 0.18 | (119013) | GCU | A | 0.26 | (202329) | GAU | D | 0.46 | (245435) | GGU | G | 0.16 | (118798) |
| GUC | V | 0.24 | (160764) | GCC | A | 0.40 | (310626) | GAC | D | 0.54 | (287040) | GGC | G | 0.34 | (250410) |
| GUA | V | 0.11 | ( 76398) | GCA | A | 0.23 | (173010) | GAA | E | 0.42 | (317703) | GGA | G | 0.25 | (180955) |
| GUG | V | 0.47 | (317359) | GCG | A | 0.11 | ( 82647) | GAG | E | 0.58 | (441298) | GGG | G | 0.25 | (180001) |

Figure 15

```
tcaatattggccattagccatattattcattggttatatagcataaatcaatattggct
attggccattgcatacgttgtatctatatcataatatgtacatttatattggctcatgt
ccaatatgaccgccatgttggcattgattattgactagttattaatagtaatcaattac
ggggtcattagttcatagcccatatatggagttccgcgttacataacttacggtaaatg
gcccgcctggctgaccgcccaacgaccccgcccattgacgtcaataatgacgtatgtt
cccatagtaacgccaatagggactttccattgacgtcaatgggtggagtatttacggta
aactgcccacttggcagtacatcaagtgtatcatatgccaagtccgcccctattgacg
tcaatgacggtaaatggcccgcctggcattatgcccagtacatgaccttacgggacttt
cctacttggcagtacatctacgtattagtcatcgctattaccatggtgatgcggttttg
gcagtacaccaatgggcgtggatagcggtttgactcacggggatttccaagtctccacc
ccattgacgtcaatgggagtttgttttggcaccaaaatcaacgggactttccaaaatgt
cgtaacaactgcgatcgcccgccccgttgacgcaaatgggcggtaggcgtgtacggtgg
gaggtctatataagcagagctcgtttagtgaaccgtcagatcactagaagctttattgc
ggtagtttatcacagttaaattgctaacgcagtcagtgcttctgacacaacagtctcga
acttaagctgcagtgactctcttaaggtagccttgcagaagttggtcgtgaggcactgg
gcaggtaagtatcaaggttacaagacaggtttaaggagaccaatagaaactgggcttgt
cgagacagagaagactcttgcgtttctgataggcacctattggtcttactgacatccac
tttgcctttctctccacaggtgtccactcccagttcaattacagctcttaaggctagag
tacttaatacgactcactataggctagcctcgagaattcacgcgtggtacctctagagt
cgacccgggcggccgcttccctttagtgagggttaatgcttcgagcagacatgataaga
tacattgatgagtttggacaaaccacaactagaatgcagtgaaaaaaatgctttatttg
tgaaatttgtgatgctattgctttatttgtaaccattataagctgcaataaacaagtta
acaacaacaattgcattcattttatgtttcaggttcaggggagatgtgggaggttttt
taaagcaagtaaaacctctacaaatgtggtaaaatccgataaggatcgatccgggctgg
cgtaatagcgaagaggcccgcaccgatcgcccttcccaacagttgcgcagcctgaatgg
cgaatggacgcgccctgtagcggcgcattaagcgcggcgggtgtggtggttacgcgcag
cgtgaccgctacacttgccagcgccctagcgcccgctcctttcgctttcttcccttcct
ttctcgccacgttcgccggctttccccgtcaagctctaaatcgggggctcccttaggg
ttccgatttagtgctttacggcacctcgaccccaaaaaacttgattagggtgatggttc
acgtagtgggccatcgccctgatagacggtttttcgccctttgacgttggagtccacgt
tctttaatagtggactcttgttccaaactggaacaacactcaaccctatctcggtctat
tcttttgatttataagggattttgccgatttcggcctattggttaaaaaatgagctgat
ttaacaaaaatttaacgcgaattttaacaaaatattaacgcttacaatttcctgatgcg
gtattttctccttacgcatctgtgcggtatttcacaccgcatacgcggatctgcgcagc
accatggcctgaaataacctctgaaagaggaacttggttaggtaccttctgaggcggaa
agaaccaggatccgcgtatggtgcactctcagtacaatctgctctgatgccgcatagtt
aagccagccccgacacccgccaacacccgctgacgcgccctgacgggcttgtctgctcc
cggcatccgcttacagacaagctgtgaccgtctccgggagctgcatgtgtcagaggttt
tcaccgtcatcaccgaaacgcgcgagacgaaagggcctcgtgatacgcctatttttata
ggttaatgtcatgataataatggtttcttagacgtcaggtggcacttttcggggaaatg
tgcgcggaacccctatttgtttatttttctaaatacattcaaatatgtatccgctcatg
agacaataaccctgataaatgcttcaataatattgaaaaaggaagagtatgagtattca
acatttccgtgtcgcccttattcccttttttgcggcattttgccttcctgtttttgctc
acccagaaacgctggtgaaagtaaaagatgctgaagatcagttgggtgcacgagtgggt
tacatcgaactggatctcaacagcggtaagatccttgagagttttcgccccgaagaacg
```

Figure 17

```
ttttccaatgatgagcacttttaaagttctgctatgtggcgcggtattatcccgtattg
acgccgggcaagagcaactcggtcgccgcatacactattctcagaatgacttggttgag
tactcaccagtcacagaaaagcatcttacggatggcatgacagtaagagaattatgcag
tgctgccataaccatgagtgataacactgcggccaacttacttctgacaacgatcggag
gaccgaaggagctaaccgcttttttgcacaacatgggggatcatgtaactcgccttgat
cgttgggaaccggagctgaatgaagccataccaaacgacgagcgtgacaccacgatgcc
tgtagcaatggcaacaacgttgcgcaaactattaactggcgaactacttactctagctt
cccggcaacaattaatagactggatggaggcggataaagttgcaggaccacttctgcgc
tcggcccttccggctggctggtttattgctgataaatctggagccggtgagcgtgggtc
tcgcggtatcattgcagcactggggccagatggtaagccctcccgtatcgtagttatct
acacgacggggagtcaggcaactatggatgaacgaaatagacagatcgctgagataggt
gcctcactgattaagcattggtaactgtcagaccaagtttactcatatatactttagat
tgatttaaaacttcatttttaatttaaaaggatctaggtgaagatccttttttgataatc
tcatgaccaaaatcccttaacgtgagttttcgttccactgagcgtcagacccgtagaa
aagatcaaaggatcttcttgagatcctttttttctgcgcgtaatctgctgcttgcaaac
aaaaaaaccaccgctaccagcggtggtttgtttgccggatcaagagctaccaactcttt
ttccgaaggtaactggcttcagcagagcgcagataccaaatactgttcttctagtgtag
ccgtagttaggccaccacttcaagaactctgtagcaccgcctacatacctcgctctgct
aatcctgttaccagtggctgctgccagtggcgataagtcgtgtcttaccgggttggact
caagacgatagttaccggataaggcgcagcggtcgggctgaacggggggttcgtgcaca
cagcccagcttggagcgaacgacctacaccgaactgagatacctacagcgtgagctatg
agaaagcgccacgcttcccgaagggagaaaggcggacaggtatccggtaagcggcaggg
tcggaacaggagagcgcacgagggagcttccaggggggaaacgcctggtatctttatagt
cctgtcgggtttcgccacctctgacttgagcgtcgattttgtgatgctcgtcagggg
gcggagcctatggaaaaacgccagcaacgcggccttttacggttcctggccttttgct
ggcctttṯgctcacatggctcgacagatct
```

Figure 17 (continued)

SYNTHETIC DNA ENCODING AN ORANGE SEAPEN-DERIVED GREEN FLUORESCENT PROTEIN WITH CODON PREFERENCE OF MAMMALIAN EXPRESSION SYSTEMS AND BIOSENSORS

BENEFIT OF PRIOR PROVISIONAL APPLICATION

This utility patent application claims the benefit of co-pending prior U.S. Provisional Patent Application Serial No. 60/297,645, filed Jun. 12, 2001, entitled "Synthetic DNA Encoding A Green Fluorescent Protein With The Most Favored Codons For Mammalian Systems" having the same named applicants as inventors, namely, Yih-Tai Chen and Longguang Cao.

BACKGROUND OF THE INVENTION

1. Field of the Invention

The present invention relates to an isolated and purified DNA encoding a humanized bioluminescent green fluorescent protein (hPtFP) derived from the orange seapen *Ptilosarcus gurneyi* in which all the codons are the favored or most favored codons for mammalian expression systems. Truncation mutants of the humanized *Ptilosarcus gurneyi* fluorescent protein (hPtFP) of the present invention are functional as fluorescent reporter molecules in a biosensor system. The green fluorescent protein of the present invention is useful as an improved fusion partner in cellular proteins allowing direct observation of the behavior of the tagged protein.

2. Description of the Background Art

A major component of the new drug discovery paradigm is a continually growing family of fluorescent and luminescent reagents that are used to measure the temporal and spatial distribution, content, and activity of intracellular ions, metabolites, macromolecules and organelles. Classes of these reagents include labeling reagents that measure the distribution and amount of molecules in living or fixed cells, environmental indicators to report signal transduction events in time and space, and fluorescent protein biosensors to measure target molecular activities within living cells. A multiparameter approach that combines several reagents in a single cell is a powerful new tool for drug discovery.

Those skilled in this art will recognize a wide variety of fluorescent reporter molecules that can be used in the field of drug discovery. Particularly, herein are disclosed novel humanized fluorescent proteins. Similarly, fluorescent reagents specifically synthesized with particular chemical properties of binding or association have been used as fluorescent reporter molecules. (Barak et al., (1997), *J. Biol. Chem.* 272:27497–27500; Southwick et al., (1990), *Cytometry* 11:418–430; Tsien (1989) in *Methods in Cell Biology*, Vol. 29 Taylor and Wang (eds.), pp. 127–156). Fluorescently labeled antibodies are particularly useful reporter molecules due to their high degree of specificity for attaching to a single molecular target in a mixture of molecules as complex as a cell or tissue. However, fluorescently labeled antibodies present several limitations.

It is known that luminescent probes can be synthesized within the living cell or can be transported into the cell via several non-mechanical modes including diffusion, facilitated or active transport, signal-sequence-mediated transport, and endocytic or pinocytic uptake. Mechanical bulk loading methods, which are well known in the art, can also be used to load luminescent probes into living cells. (Barber et al. (1996), Neuroscience letters 207:17–20; Bright et al. (1996), *Cytometry* 24:226–233; McNeil (1989) in *Methods in Cell Biology*, Vol. 29, Taylor and Wang (eds.) pp. 153–173). These methods include electroporation and other mechanical methods such as scrape-loading, bead-loading, impact loading, syringe-loading, hypertonic and hypotonic loading. Additionally, cells can be genetically engineered to express reporter molecules such as Green Fluorescent Protein, coupled to a protein of interest as previously described (Chalfie and Prasher U.S. Pat. No. 5,491,084; Cubitt et al. (1995), *Trends in Biochemical Science*, 20:448–455).

Luminescence is the process whereby a molecule is electronically excited and releases light when it returns to a lower energy state. Bioluminescence is the process by which living organisms emit light that is visible to other organisms. In bioluminescence the excited state is created by an enzyme-catalyzed reaction. The color of the emitted light in a bioluminescent reaction is characteristic of the excited molecule, and is independent from its source of excitation and temperature.

Molecular oxygen is known to be essential in some well characterized bioluminescent systems, such as the bioluminescence of luciferase. Luciferases are oxygenases, that act on a substrate, luciferin, in the presence of molecular oxygen and transform the substrate to an excited state. Upon return to a lower energy level, energy is released in the form of light. Ward et al., Chapter 7 in *Chemi-and Bio-luminescence*, Burr ed. Marcel Dekker, Inc. NY, pp. 321–358; Hastings, J. W. (1995) *Cell Physiology: Source Book*, N. Sperelakis (ed.), Academic Press, pp. 665–681; *Luminescence, Narcosis and Life in the Deep Sea*, Johnson Vantage Press, NY, pp. 50–56. Bioluminescent species span many genera and include microscopic organisms, including bacteria, primarily marine bacteria such as Vibrio species, fungi, algae, and dinoflagellates, to marine organisms including arthropods, mollusks, echinoderms, and chordates, and terrestrial organisms including annelids and insects.

Luminescence (bioluminescence, chemiluminescence, and fluorescence) is used for qualitative and quantitative determination of specific substances and processes in biology and medicine. For example, various luciferase genes from various organisms have been cloned and exploited as reporters in numerous assays. On the other hand, treating cells with dyes and fluorescent biomolecules allowing imaging of the cells, and genetic engineering of cells to produce fluorescent proteins as reporter molecules are useful detection methods known by those persons skilled in the art. For instance, treating cells with dyes and fluorescent biomolecules allowing imaging the cells, and genetic engineering of cells to produce fluorescent proteins as reporter molecules are useful detection methods known in the art. Wang et al., *Methods in Cell Biology*, New York, Alan R. Liss, 29:1–12, 1989. One such fluorescent reporter protein is the green fluorescent protein (GFP) of the jellyfish *Aequorea* Victoria which absorbs blue light with an excitation maximum at 395 nm, with a minor peak at 470 nm, and emits green fluorescence with an emission maximum at 510 nm, with a minor peak near 540 nm and does not require an exogenous factor. However, the absorption and emission spectra for Aequorea GFP present certain limitations. The excitation and emission maxima of the wild type Aequorea GFP are not within the optimal range of wavelengths of standard fluorescence optics.

The green fluorescent proteins (GFP) constitute a class of chromoproteins found among certain bioluminescent coelenterates. These proteins are fluorescent and function as the ultimate bioluminescence emitter in these organisms by accepting energy from enzyme-bound, excited state oxyluciferin. Ward et al., (1982) *Biochemistry* 21: 4535–4540.

Uses of Aequora GFP for the study of gene expression and protein localization are discussed in Chalfie et al., *Science* 263:802–805, 1994. Some properties of wild-type Aequora GFP are disclosed by Morise et al., *Biochemistry* 13:2656–2662, 1974, and Ward et al., *Photochem. Photobiol.* 31:611–615, 1980. An article by Rizzuto et al., *Nature* 358:325–327, 1992, discusses the use of wild-type Aequora GFP as a tool for visualizing subcellular organelles in cells. Kaether and Gerdes, *FEBS Letters* 369:267–271, 1995, report the visualization of protein transport along the secretory pathway using wild-type Aequora GFP. The expression of Aequora GFP in plant cells is discussed by Hu and Cheng, *FEBS Letters* 369:331–334, 1995, while Aequora GFP expression in Drosophila embryos is described by Davis et al., *Dev. Biology* 170:726–729, 1995.

U.S. Pat. No. 5,491,084 discloses expression of GFP from *Aequorea victoria* in cells for use as a reporter molecule fused to another protein of interest. PCT/DK96/00052 relates to methods of detecting biologically active substances affecting intracellular processes by utilizing a GFP construct having a protein kinase activation site. GFP proteins are used in various biological systems. For example, PCT/US95/10165 describes a system for isolating cells of interest utilizing the expression of a GFP-like protein. PCT/GB96/00481 describes the expression of GFP in plants. PCT/US95/01425 describes modified GFP protein expressed in transformed organisms to detect mutagenesis. Mutants of GFP have been prepared and used in several biological systems. (Hasselhoff et al., *Proc. Natl. Acad. Sci.* 94:2122–2127, 1997; Brejc et al., *Proc. Natl. Acad Sci.* 94:2306–2311, 1997; Cheng et al., *Nature Biotech.* 14:606–609, 1996; Heim and Tsien, *Curr. Biol.* 6:178–192, 1996; Ehrig et al., *FEBS Letters* 367:163–166, 1995). Methods describing assays and compositions for detecting and evaluating the intracellular transduction of an extracellular signal using recombinant cells that express cell surface receptors and contain reporter gene constructs that include transcriptional regulatory elements that are responsive to the activity of cell surface receptors are disclosed in U.S. Pat. No. 5,436,128 and U.S. Pat. No. 5,401,629.

Certain types of cells within an organism may contain components that can be specifically labeled that may not occur in other cell types. For example, epithelial cells often contain polarized membrane components. That is, these cells asymmetrically distribute macromolecules along their plasma membrane. Connective or supporting tissue cells often contain granules in which are trapped molecules specific to that cell type (e.g. heparin, histamine, serotonin, etc.) Skeletal muscle cells contain a sarcoplasmic reticulum, a specialized organelle whose function is to regulate the concentration of calcium ions within the cell cytoplasm. Many nervous tissue cells contain secretory granules and vesicles in which are trapped neurohormones or neurotransmitters. Therefore, fluorescent molecules can be designed to label not only specific components within specific cells, but also specific cells within a population of mixed cell types.

Those skilled in the art will recognize a wide variety of ways to measure fluorescence. For example, some fluorescent reporter molecules exhibit a change in excitation or emission spectra, some exhibit resonance energy transfer where one fluorescent reporter loses fluorescence, while a second gains in fluorescence, some exhibit a loss (quenching) or appearance of fluorescence, while some report rotational movements. (Giuliano et al. (1995), *Ann.*  *Rev. of Biophysics and Biomol. Structure* 24:405–434; Giuliano et al. (1995), *Methods in Neuroscience* 27:1–16). The GFPs exhibit absorption at a particular wavelength, and emission at a different wavelength characteristic for each green fluorescent protein which sometimes allows for the pairing of GFP's with two distinct signals being detectable.

In addition to the limitations in detection with standard fluorescence optics presented by the absorption-emission wavelength spectrum of Aequora GFP, another difficulty is the potentially low level of fluorescent signal emitted by GFP transfected into a heterologous cell type. This is the result of low level expression normally associated with the expression of a non-native species protein being expressed by a cell, in this case a jellyfish protein being expressed in higher level organisms such as mammals. This is partly due to different codon usage in the native marine organism sequences that are different from the host or transfected cell's codon usage. In spite of this background art, there remains a very real and substantial need for a fluorescent reporter molecule having a narrower absorption-emission wavelength spectrum and having an optimized expression in a host or transfected cell resulting in fluorescent signals that are easily detected with standard fluorescence optics.

U.S. Pat. Nos. 5,786,464 (Seed et al.) and 5,795,737 (Seed et al.) disclose replacing non-preferred codons with preferred codons to increase expression in mammalian cell lines of other proteins, such as the green fluorescent protein of the jellyfish *Aequorea Victoria*.

U.S. Pat. No. 5,874,304 (Zolotukhin et al.) discloses a humanized green fluorescent protein gene adapted from the jellyfish *Aequorea Victoria*. U.S. Pat. No. 5,968,750 (Zolotukhin et al.) discloses a method of labeling a mammalian cell comprising expressing a humanized green fluorescent protein gene in the cell wherein the genes have an increased number of GCC or GCT alanine-encoding codons in comparison to the wild type jellyfish gene sequence.

U.S. Pat. No. 6,232,107 (Bryan et al.) discloses isolated and purified nucleic acids encoding green fluorescent proteins from the genus Renilla and Ptilosarcus and the green fluorescent proteins encoded thereby.

BRIEF DESCRIPTION OF THE DRAWINGS

FIG. 1 shows comparative fluorescence of COS1 cells expressing the synthetic DNA versus a commercially available nuclear dye (Hoechst 33342 stain).

FIG. 4 shows two examples of the stable cell lines established by transfection with hPtFP green fluorescent protein DNA of the present invention. The left panel shows stable A549 cells transfectants expressing hPtFP. The right panel shows stable HEK293 cell transfectants expressing hPtFP.

FIG. 6, Panel A, shows COS1 cells transiently transfected with human CD7 and were stained with a monoclonal antibody against human CD7. Panels B & C show COS1 cells transiently transfected with CD7-fluorescent protein.

FIG. 9 shows the wild type *Ptilosarcus gurneyi* nucleotide sequence (top row) compared to the nucleotide sequence encoding the humanized *Ptilosarcus gurneyi* fluorescent protein of the present invention (bottom row).

FIG. 10 shows the amino acid sequence (top row) and the double stranded nucleotide sequence (bottom rows) of the humanized *Ptilosarcus gurneyi* fluorescent protein of the present invention.

FIG. 11 shows the full length nucleotide of humanized *Ptilosarcus gurneyi* fluorescent protein of the present invention including regions upstream and downstream to the coding region.

FIG. 12 shows the full length protein sequence of humanized *Ptilosarcus gurneyi* fluorescent protein of the present invention from start codon to stop codon.

FIG. 13 shows the (truncated) deletion mutants of hPtFP and their effects on green fluorescence.

FIG. 14 shows HeLa cells transfected with the hPtFP-Caspase-8 biosensor of this invention before and after treatment with staurosporine.

FIG. 15 shows a codon usage table for a human system, compiled from 22747 coding regions CDS's (10965560 codons).

FIG. 17 shows the nucleotide sequence of expression vector M2.

SUMMARY OF THE INVENTION

Figure 2:
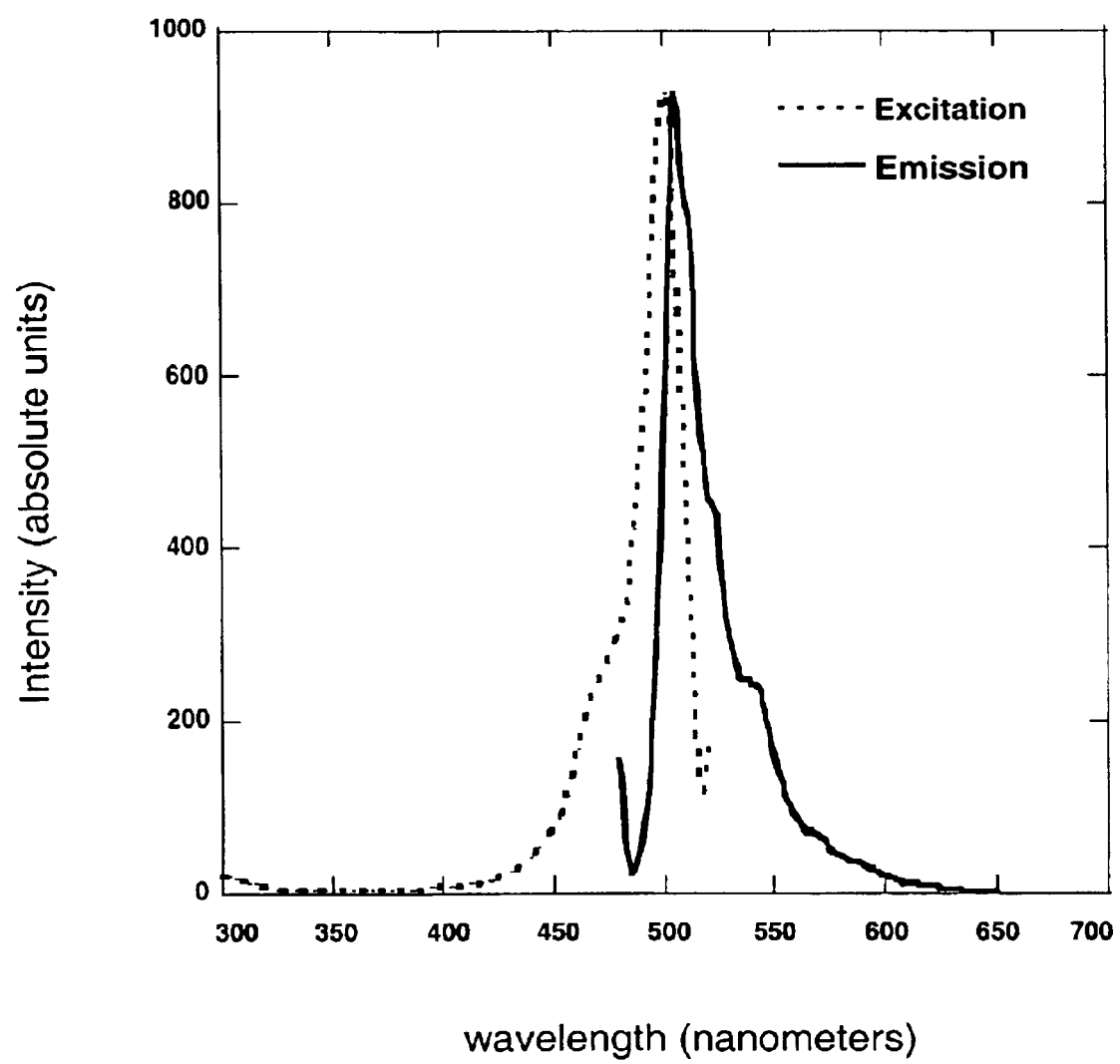
FIG. 2 shows in situ fluorescence of the humanized *Ptilosarcus gurneyi* fluorescent protein in COS1 cells.

The present invention has met the hereinbefore described needs. The present invention provides an isolated and purified DNA encoding a green fluorescent protein from the orange seapen *Ptilosarcus gurneyi* in which all of the codons are favored for mammalian systems. The full length encoded protein of the present invention has 239 amino acid residues. Preferably, the encoded protein of the present invention is truncated having 224 amino acid residues and most preferably has 219 amino acid residues. In comparison to the wild type *Ptilosarcus gurneyi* green fluorescent protein having 238 amino acid residues, codons for 145 amino acids of the humanized *Ptilosarcus gurneyi* green fluorescent protein of the present invention were changed based on human codon bias.

The encoded protein of the present invention, when expressed in mammalian cell lines gives strong green fluorescence.

The synthetic DNA of the present invention can be used as a fluorescent tag for monitoring the activities of fusion partners using known image based techniques.

DETAILED DESCRIPTION OF THE INVENTION

The present invention provides a synthetic cDNA, based on the orange seapen *Ptilosarcus gurneyi* green fluorescent protein sequence, to encode a green fluorescent protein in which the majority of the codons are the favored or the most favored codons for mammalian expression systems. This process of codon preference modification when going from a native species to a host species, especially of going into a human cell-line host, is called "humanization".

A humanized gene is one that has been adapted for expression in human cells by replacing at least one, and most preferably, a significant number of the codons in the native gene codons with codons that are most frequently used in human gene expression. Thus, the native codon usage is replaced with a codon that is more favorable for translation in a human or mammalian cell line. One reason for low expression of foreign genes in mammalian expression systems is the poor translation efficiency of the mRNA in the mammalian, and especially human cell environment. The reason for this is the difference in abundance of particular isoacceptor tRNA's that are different in human cells than those found in other organisms. In this instance the isoacceptor tRNA's are different in the *Ptilosarcus gurneyi* orange seapen than in human cells. Making the codon usage in the foreign gene match the prevalent isoacceptor tRNA subpopulation leads to improved translation efficiency, thus improved expression of the foreign gene in human cells.

The use of codon preference modification at the cDNA level results in higher levels of expression of the modified DNA molecule. Higher levels of expression leads to higher protein yield thus higher fluorescent signal in mammalian cells expressing the modified cDNA. The encoded protein of the present invention has 239 amino acid residues. In comparison to the wild type *Ptilosarcus gurneyi* green fluorescent protein (238 amino acid residues), codons for 145 amino acids were changed based on human codon preferences. One amino acid (valine) was added at the amino terminus to be the second amino acid residue in this protein. The encoded protein, when expressed in mammalian cell lines, gives strong green fluorescence. Generally, the green fluorescence to be achieved by the present invention is the production of light visible to the naked eye for qualitative purposes. Thus, the amount of the component of the bioluminescence reaction need not be stringently determined or met. It must be sufficient to produce light. The synthetic DNA of the present invention can be used as a fluorescent tag for monitoring the activities of its fusion partner, as described herein, using known imaging based approaches.

Figure 18:
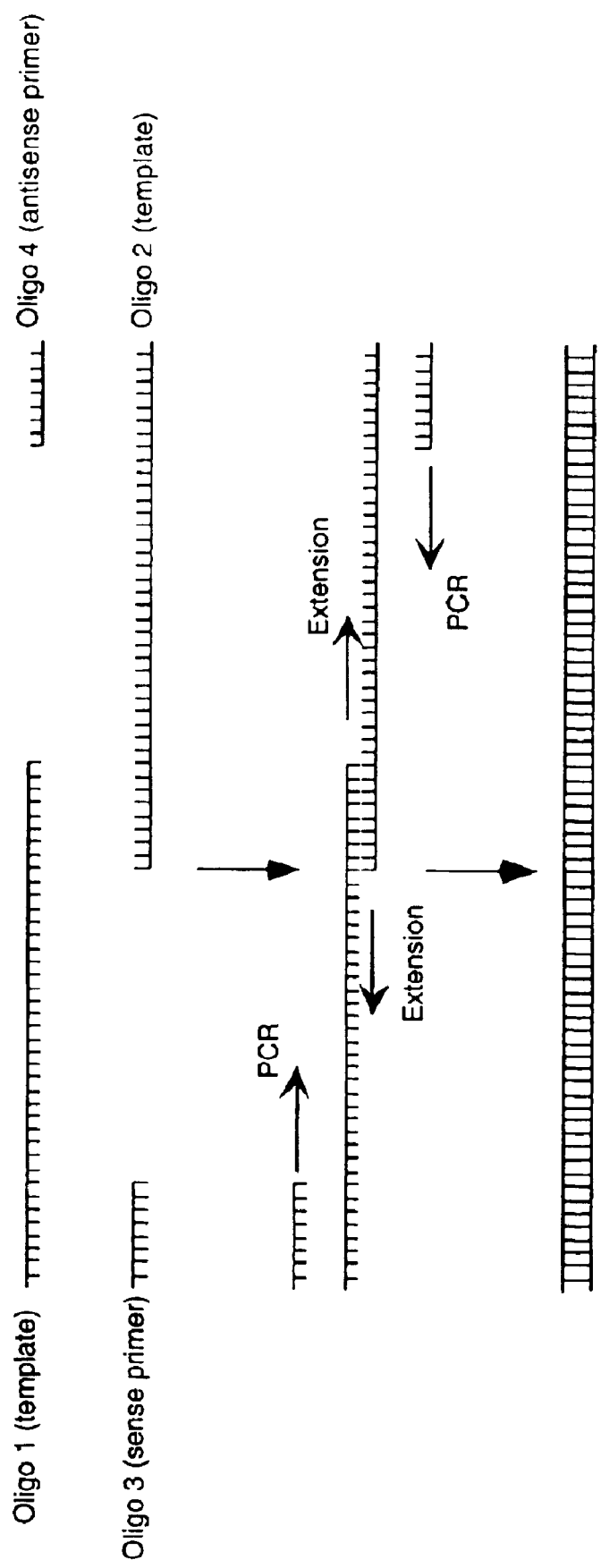
FIG. 18 shows a general description of gene synthesis.

As will be appreciated by those skilled in the art, gene synthesis is performed by piecing together small pieces of double-stranded synthetic DNA. Each small double-stranded synthetic DNA is pieced together with even smaller single-stranded oligonucleotides. To place together one piece of the double-stranded DNA, 4 oligonucleotides are required. FIG. 18 shows oligo 1 and oligo 2 are complimentary to each other in part of them. Thus, they can anneal to each other and can be extended by a DNA polymerase, such as for example Taq polymerase. The extended template then works as the template for an amplification reaction (using, for example. Taq polymerase) employing oligo 3 and oligo 4 as the sense and anti-sense primers, respectively. The extension of the template and the amplification reaction are actually performed at the same time in the same test tube, and thus no separate step is shown in FIG. 18. Two pieces of double-stranded synthetic DNA, from a synthesis scheme as for example the synthesis scheme set forth in FIG. 18, may serve as the template for a new round of synthesis as long as they contain an overlapping region that can anneal to each other. This process may be repeated several times in order to create a long synthetic gene that can not be synthesized in one step. See J Hass et al., *Codon usage limitation in the expression of HIV-1 envelope glycoprotein*, Curr. Biol., Vol 6 (3), pages 315–324 (March 1996).

The fluorescent protein encoded by the modified humanized cDNA of the present invention is substantially identical to the wild type *Ptilosarcus gurneyi* fluorescent protein at the amino acid level, with the exception that the present invention provides for the addition of a single valine residue at position number 2 from the amino terminus. The absorption and emission spectra of the hPtFP in COS-1 cells was unchanged as compared to the wildtype *Ptilosarcus gurneyi*.

FIG. 10 shows the double stranded nucleotide sequence (bottom two rows) of the entire coding region and the deduced amino acid sequence (top row) of the humanized *Ptilosarcus gurneyi* fluorescent protein (hereinafter "hPtFP") of the present invention, as well as the start and stop codon sequence, untranslated regions and restriction sites. FIG. 11 shows the full length coding sequence of hPtFP of the present invention including regions upstream and downstream to the coding region.

FIG. 12 shows the full length coding sequence of the hPtFP of the present invention from start codon to stop codon. Thus the total length of the humanized *Ptilosarcus gurneyi* fluorescent protein (hPtFP) of the present invention is 239 amino acid residues versus 238 for the wild type *Ptilosarcus gurneyi* fluorescent protein (PtFP). It will be appreciated that at the nucleotide level, approximately 61% of the wild type codons have been changed based on human codon bias. FIG. 15 shows the codon usage table for human system, compiled from 22747 CDS's (10965560 codons) based on GenBank Release 118.0 (Jun. 15, 2000), obtained from Kazusa DNA Research Institute (Japan). FIG. 15 shows the following fields: [triplet] [amino acid] [fraction, % of gene using the particular codon] [number of codons examined].

Figure 16:
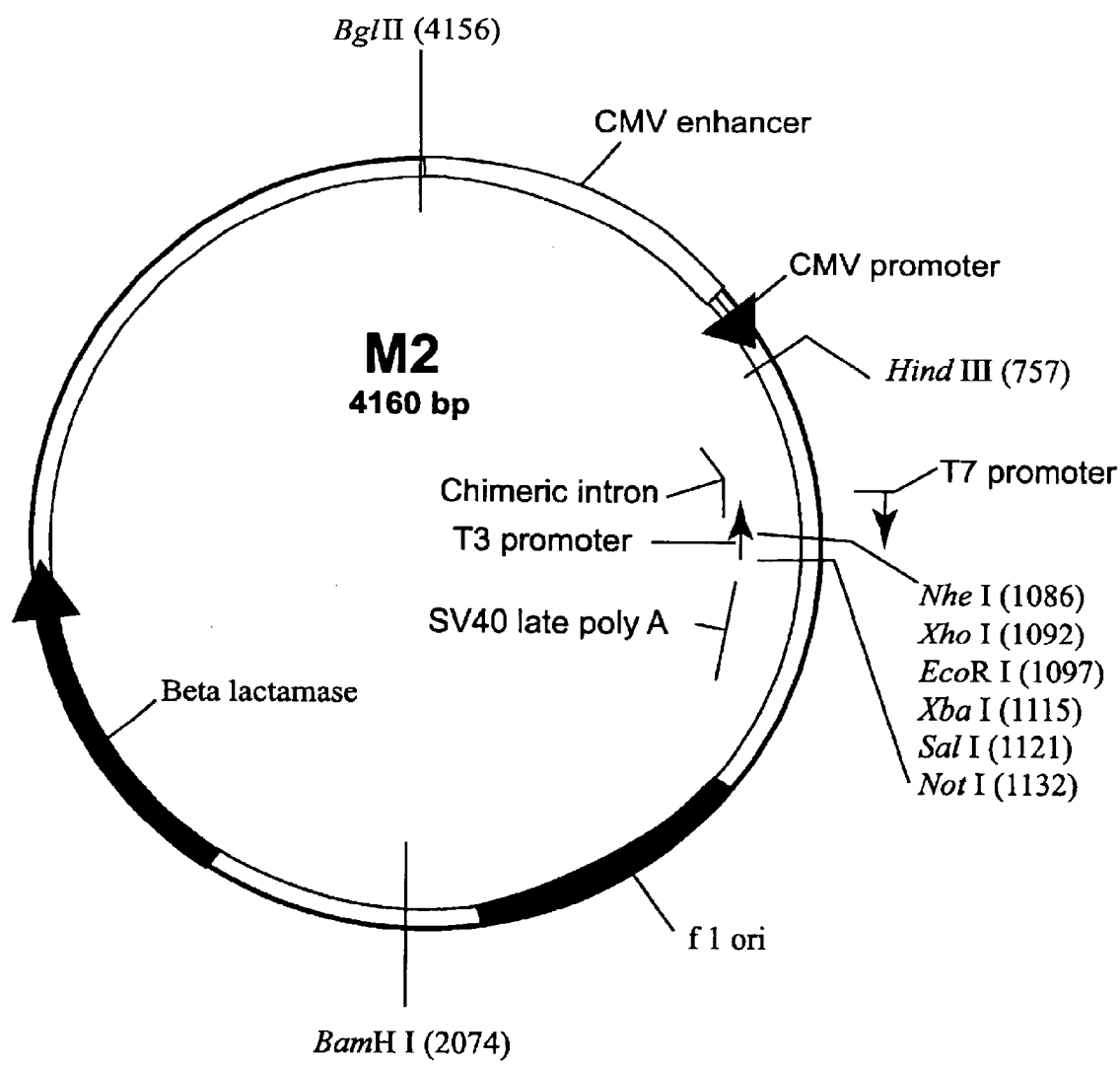
FIG. 16 shows a restriction endonuclease cleavage map for expression vector M2.

FIG. 9 shows the wild type *Ptilosarcus gurneyi* (PtFP) nucleotide sequence (top row) compared to the nucleotide sequence (bottom row) encoding the hPtFP of the present invention. The difference at the nucleotide level (versus codon level) is that the hPtFP open reading frame (including the stop codon) contains 720 nucleotides, whereas the PtFP open reading frame (including the stop codon) contains 717 nucleotides. It will be appreciated by those skilled in the art, that without counting the extra valine introduced into hPtFP of the present invention, there are 166 nucleotide differences between the 717 nucleotides compared, or 23.15 percent difference (or 76.85% identity). If the stop codon is excluded in this comparison, there are 165 nucleotide differences in the 714 nucleotides compared, or 23.10 percent difference (or 76.9% identity). The synthetic DNA of the present invention was subcloned into an expression vector M2 (Cellomics, Inc., Pittsburgh, Pa., USA) after restriction digestion of both DNAs with HindIII (New England Biolabs, Inc., Beverly, Mass., USA) and NotI (New England Biolabs, Inc., Beverly, Mass., USA) restriction endonucleases. The resulting expression vector was then used to transfect COS1 cells (CRL-1650, American Type Culture Collection [ATCC], Manassas, Va., USA) using FUGENE 6 transfection reagent (Roche Molecular Biochemicals, Indianapolis, Ind., USA) following the protocol supplied by the manufacturer. FIG. 16 shows an restriction endonuclease cleavage map of M2. FIG. 17 shows the coding sequence of M2. M2 is a derivative of pCI-neo (Promega, Madison, Wis., USA). Forty-eight (48) hours post transfection, the fluorescence was observed with an inverted epi-fluorescent microscope using a filter set for observing fluorescence as set forth in FIG. 1. FIG. 1 shows the expression of hPtFP in COS1 cells transiently transfected with the synthetic DNA of the present invention (right panel). The cells were counter stained with Hoechst 33342 (Molecular Probes, Eugene, Oreg., USA), a nuclear stain, FIG. 1 (left panel).

Forty-eight hours after initial transfection with the synthetic green fluorescent protein DNA of the present invention, COS1 cells were trypsinized and were kept in suspension. The absorption and emission spectra of the live cells expressing the hPtFP of the present invention were then measured, as shown in FIG. 2. FIG. 2 shows the in situ fluorescence of the humanized *Ptilosarcus gurneyi* fluorescent protein (hPtFP) in COS1 cells.

Figure 3:
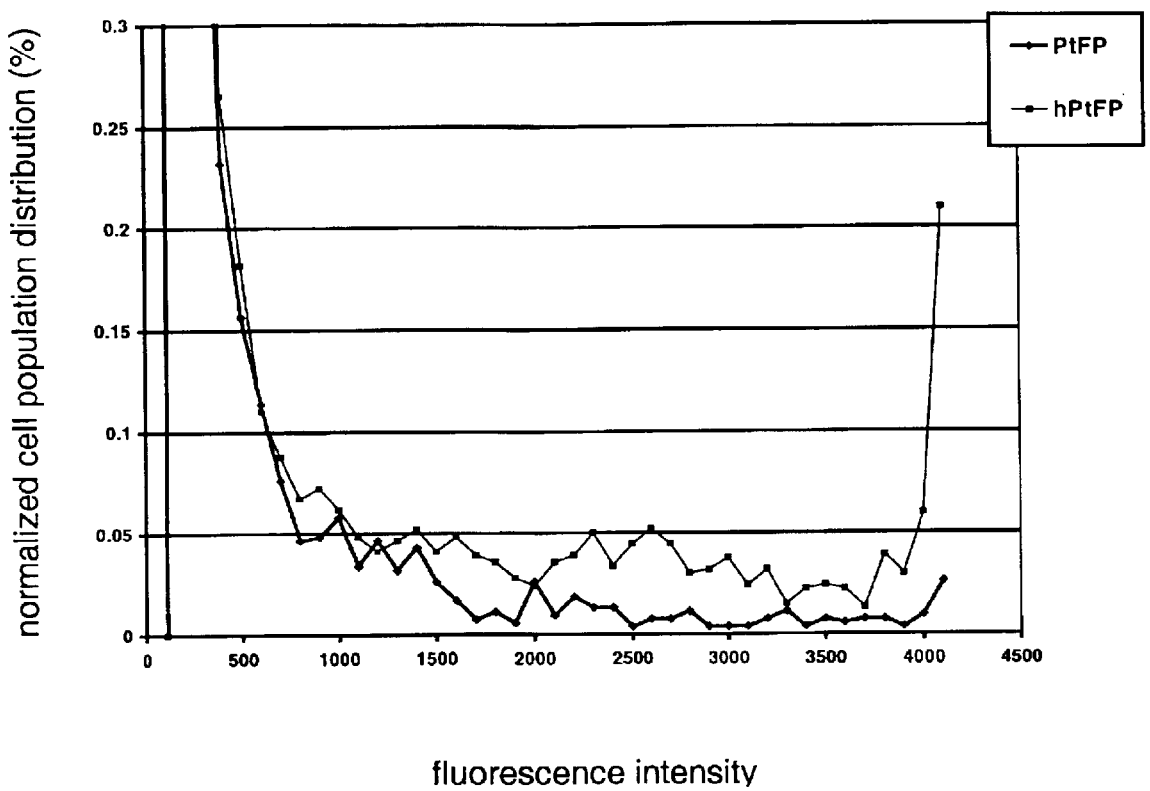
FIG. 3 is a histogram of the fluorescent intensity in COS1 cells transiently transfected with wild type *Ptilosarcus gurneyi* green fluorescent protein DNA or the synthetic green fluorescent protein DNA. The X-axis of FIG. 3 is the fluorescence intensity, minimum is zero and maximum is 4095. The Y-axis of FIG. 3 is the normalized distribution (percentage) of the cell population.

To compare the expression of wild type *Ptilosarcus gurneyi* fluorescent protein DNA with humanized *Ptilosarcus gurneyi* green fluorescent protein synthetic DNA as described above, an expression vector for the wild type *Ptilosarcus gurneyi* DNA was constructed by cloning the wild type PtFP into the expression vector M2, and thus, these two expression vectors under comparison differed only in their coding regions. Both DNA constructs were purified using QIAGEN plasmid kit (QIAGEN Inc., Valencia, Calif., USA) following the instructions supplied by the manufacturer. The purified DNA preps were quantitated by reading the optic absorption at 260 nm (nanometers) with a HP8453 UV—visible spectrophotometer (Agilent Technologies, Palo Alto, Calif., USA) and calculated based on 1 O.D.=50 ng (nanograms) DNA. An identical amount of wild type *Ptilosarcus gurneyi* fluorescent protein DNA and the hPtFP was used to transfect COS1 cells, respectively, under identical conditions using FUGENE6 reagent, as described above. Forty hours post-transfection cells were fixed with 3.7 percent formaldehyde in the presence of 10 micrograms/milliliter of Hoechst 33342 (Molecular Probes, Eugene, Oreg., USA). The fluorescent images of the cells were then acquired using ARRAYSCAN II instrument (Cellomics, Inc., Pittsburgh, Pa., USA) with 10× objective and filter setting at "FITC broad" (excitation=365+/−25 nm, emission=450+/−30 nm for Hoechst 33342—for fluorescent stain of nuclei, and excitation=475+/−20 nm, emission=535+/−22.5 nm for hPtFP). U. S. Pat. No. 5,989,835 describes the ARRAYSCAN II optical system and is incorporated by reference herein. The acquired images were then analyzed using a desktop client of ARRAYSCAN II instrument by identifying the nuclear region, and the intensity of the hPtFP was measured in the identified nuclear area. FIG. 3 shows the comparative fluorescence measurements of COS1 cells transfected with the humanized cDNA of the present invention and the wild type cDNA. FIG. 3 shows that the synthetic *Ptilosarcus gurneyi* green fluorescent protein DNA of the present invention emits stronger fluorescent signals than the wild type *Ptilosarcus gurneyi* green fluorescent protein. The results shown in FIG. 3 confirm the Applicant's visual observation (qualitative) that the hPtFP DNA of the present invention produces more hPtFP expressing cells and brighter cells than the wild type "PtFP" DNA in transient transfection.

The humanized synthetic DNA does not have toxic effects on the host cells, which aids in its increased stable expression. Stable expression of the hPtFP of the present invention was achieved in HEK293 (CRL-1573 ATCC, Manassas, Va., USA) and A549 (CCL-185, ATCC, Manassas, Va., USA) cell lines. The cells were co-transfected with the hPtFP construct and pSV2-neo (Cat #37149, ATCC, Manassas, Va., USA) with FUGENE 6 transfection reagent (Roche Molecular Biochemicals, Indianapolis, Ind., USA) following the manufacturer's instructions. Two days after transfection, cells were treated with 0.4 mg/ml (milligram/milliliter) G418 in normal growth medium. After treating with G418 for two weeks, drug resistant cells were isolated or pooled. A mixture of stably transfected HEK293 mixed population (in which about 30% of the cells expressing hPtFP of this invention) were plated out in 96 cell micro plates. After 2, 4, or 6 days incubation, the cells were fixed with 3.7% formaldehyde for 20 minutes at room temperature (25° Centigrade). The percentage of positive cells was quantitated with ARRAYSCAN II instrument, as described herein.

Figure 5:
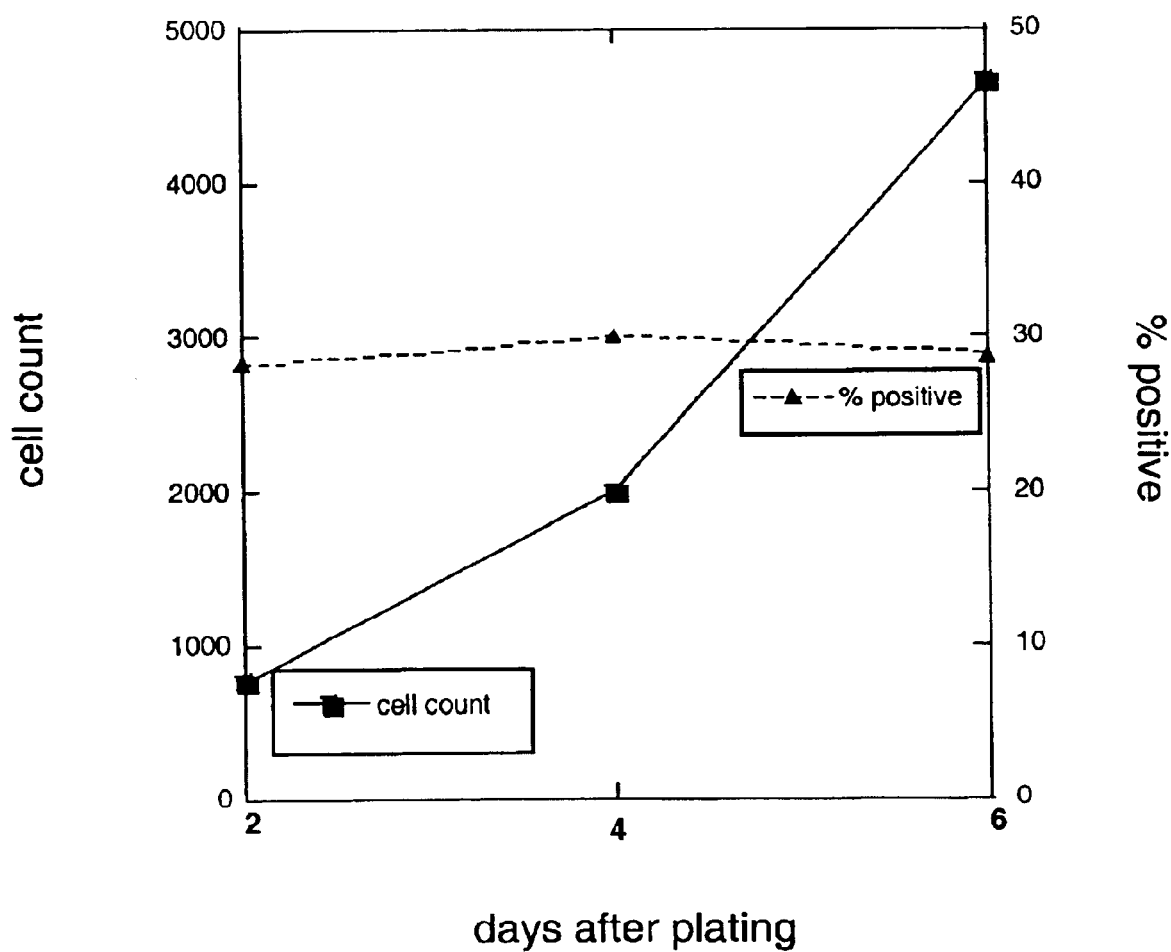
FIG. 5 shows the non toxic effect of hPtFP on its mammalian host cells.

FIG. 4, left panel, shows stably transfected HEK293 cells expressing the hPtFP of the present invention, and the right panel shows stably transfected A-549 cells. To compare the growth rates of cells expressing or not expressing hPtFP, a mixture of stably transfected HEK293 mixed population (in which about 30% of the cells expressing hPtFP of this invention) were plated out in 96-well micro plates. After 2, 4, or 6 days incubation, the cells were fixed with 3.7% (percent) formaldehyde for twenty minutes at room temperature (25 degrees Centigrade). The percentage of positive cells was quantitated with ARRAYSCAN II instrument, as described herein. FIG. 5 shows the quantitation of positive cells from a mixture of stably transfected HEK293 cell population wherein approximately thirty percent (30%) of the cells expressing hPtFP were plated and incubated as described above. FIG. 5 shows that the percentage of positive cells did not change during cell passage under no selection, indicating that the expression of the humanized *Ptilosarcus gurneyi* fluorescent protein of this invention is not toxic to the cells.

The hPtFP of this invention is useful as a fusion partner for tagging purposes. The hPtFP of this invention was fused to a model type-I single span transmembrane protein, human CD7 linked to the reactant target domain of the C-terminus of CD7. Human CD7 is a type-I single span transmembrane protein. CD7 is a member of the immunoglobulin gene superfamily well known by those skilled in the art and is a reliable clinical marker of T-cell acute lymphocytic leukemia. The fusion protein was expressed in COS1 cells by transient transfection using FUGENE 6 reagent, described hereinbefore, following the protocol supplied by the manufacturer. The distribution of the chimeric protein is similar to CD7 (no fusion partner) when transiently expressed by COS1 cells.

FIG. 6, Panel A, shows COS1 cells transiently transfected with human CD7 and stained with a monoclonal antibody against human CD7 (CD7 Ab-2, clone 124-1D1, Labvision Corp., Freemont, Calif., USA). FIG. 6, Panels B and C show COS1 cells transiently transfected with CD7-hPtFP of this invention. Panel B shows staining using a monoclonal antibody against human CD7 and Panel C shows a direct observation of the CD7-hPtFP fusion protein. The CD7-hPtFP chimera exhibits comparable localization as the untagged CD7.

The hPtFP is also useful in constructing biosensor systems. For example, the hPtFP may be used to construct protease biosensors for which the basic principle of the protease biosensors is to spatially separate the reactants from the products generated during a proteolytic reaction. The separation of products from reactants occurs upon proteolytic cleavage of the protease recognition site within the biosensor, allowing the products to bind to, diffuse into, or be imported into compartments of the cell different from those of the reactant. This spatial separation provides a means of quantitating a proteolytic process directly in living or fixed cells. A design of the biosensor provides a means of restricting the reactant (uncleaved biosensor) to a particular compartment by a protein sequence ("reactant target sequence") that binds to or imports the biosensor into a compartment of the cell. These compartments include, but are not limited to any cellular substructure, macromolecular cellular component, membrane-limited organelles, or the extra-cellular space. Given that the characteristics of the proteolytic reaction are related to product concentration divided by the reactant concentration, the spatial separation of products and reactants provides a means of uniquely quantitating products and reactants in single cells, allowing a more direct measure of proteolytic activity.

The molecular based biosensors may be introduced into cells via transfection and the expressed chimeric proteins analyzed in transiently transfected cell populations or stable cell lines. They may also be pre-formed, for example by production in a prokaryotic or eukaryotic expression system, and the purified protein introduced into the cell via a number of physical mechanisms including, such as for example, but not limited to, micro-injection, scrape loading, electroporation, and signal-sequence mediated loading, etc.

Measurement modes may include, such as for example, but are not limited to, the ratio or difference in fluorescence, luminescence, or phosphorescence: (a) intensity; (b) polarization; or (c) lifetime, between reactant and product. These latter modes require appropriate spectroscopic differences between products and reactants. For example, cleaving a reactant containing a limited-mobile signal into a very small translocating component and a relatively large non-translocating component may be detected by polarization. Alternatively, significantly different emission lifetimes between reactants and products allow detection in imaging and non-imaging modes.

One example of a family of enzymes for which this biosensor can be constructed to report activity is the caspase family. Caspases are a class of proteins that catalyze proteolytic cleavage of a wide variety of targets during apoptosis. Following initiation of apoptosis, the Class II "downstream" caspases are activated and are the point of no return in the pathway leading to cell death, resulting in cleavage of downstream target proteins. Specifically, the biosensors described herein are engineered to use nuclear translocation of cleaved hPtFP as a measurable indicator of caspase activation. Additionally, the use of specific recognition sequences that incorporate surrounding amino acids involved in secondary structure formation in naturally occurring proteins may increase the specificity and sensitivity of this class of biosensor.

The protein biosensors herein disclosed can be adapted to report the activity of any member of the caspase family of proteases, as well as any other protease, by a substitution of the appropriate protease recognition site in any of the constructs. These biosensors can be used to detect in vivo activation of enzymatic activity and to identify specific activity based on cleavage of a known recognition motif. This screen can be used for both live cell and fixed end-point assays, and can be combined with additional measurements to provide a multi-parameter assay, as is well known in the art.

Thus, another aspect of the present invention provides recombinant nucleic acids encoding a protease biosensor, comprising: (a) a first nucleic acid sequence encoding a *Ptilosarcus gurneyi* green fluorescent protein having its codon usage optimized for expression in human cells that encodes at least one detectable polypeptide signal; (b) a second nucleic acid sequence that encodes at least one protease recognition site, wherein the second nucleic acid sequence is operatively linked to the first nucleic acid sequence that encodes at least one detectable polypeptide signal; and (c) a third nucleic acid sequence that encodes at least one reactant target sequence, wherein the third nucleic acid sequence is operatively linked to the second nucleic acid sequence that encodes at least one protease recognition site.

Generally, a protease biosensor is composed of multiple domains, including at least a first detectable polypeptide signal domain, at least one reactant target domain, and at least one protease recognition domain, wherein the detectable signal domain and the reactant target domain are separated by the protease recognition domain. Thus, the exact order is not generally critical as long as the protease recognition domain separates the reactant target and first detectable signal domain. For each domain, one or more of the specified sequences is present.

Figure 7:
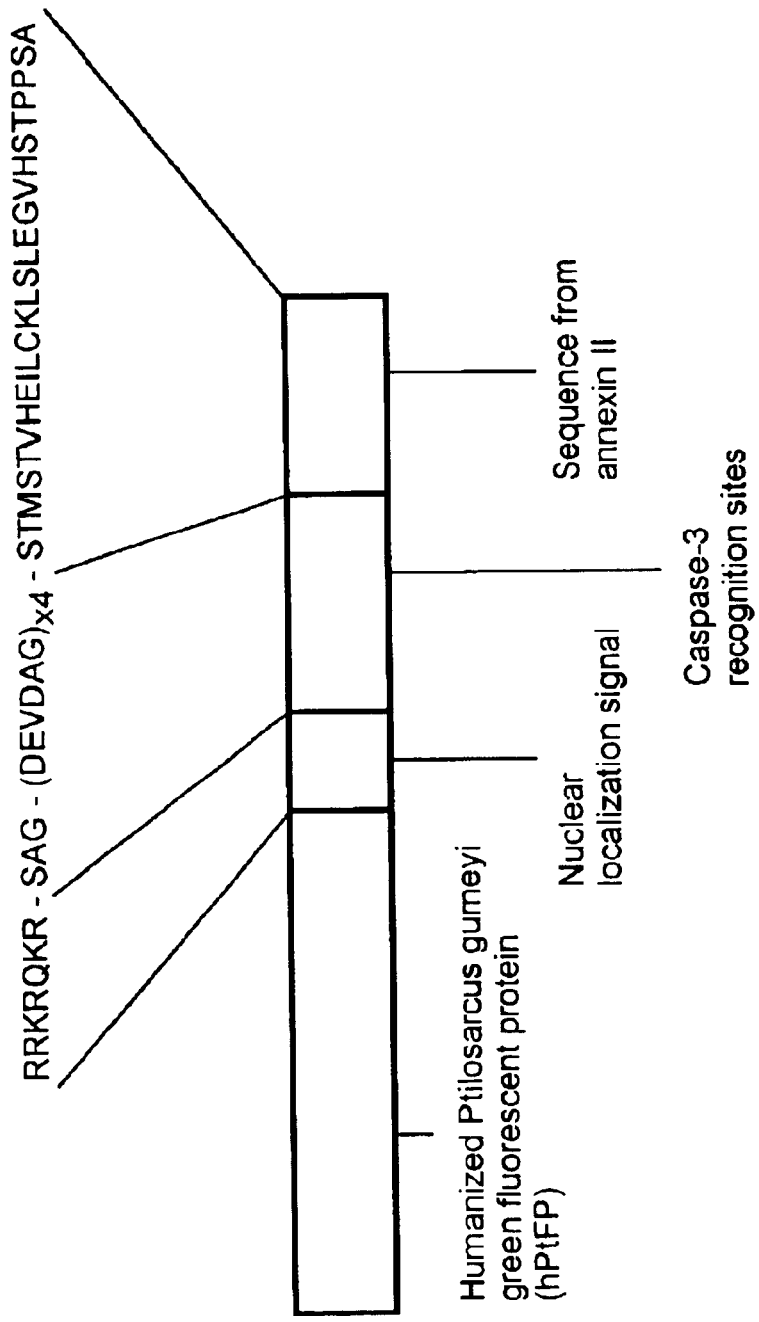
FIGS. 7 and 8 show a diagram of the configuration of the Caspase 3 and Caspase 8 biosensors, respectively.
Figure 8:
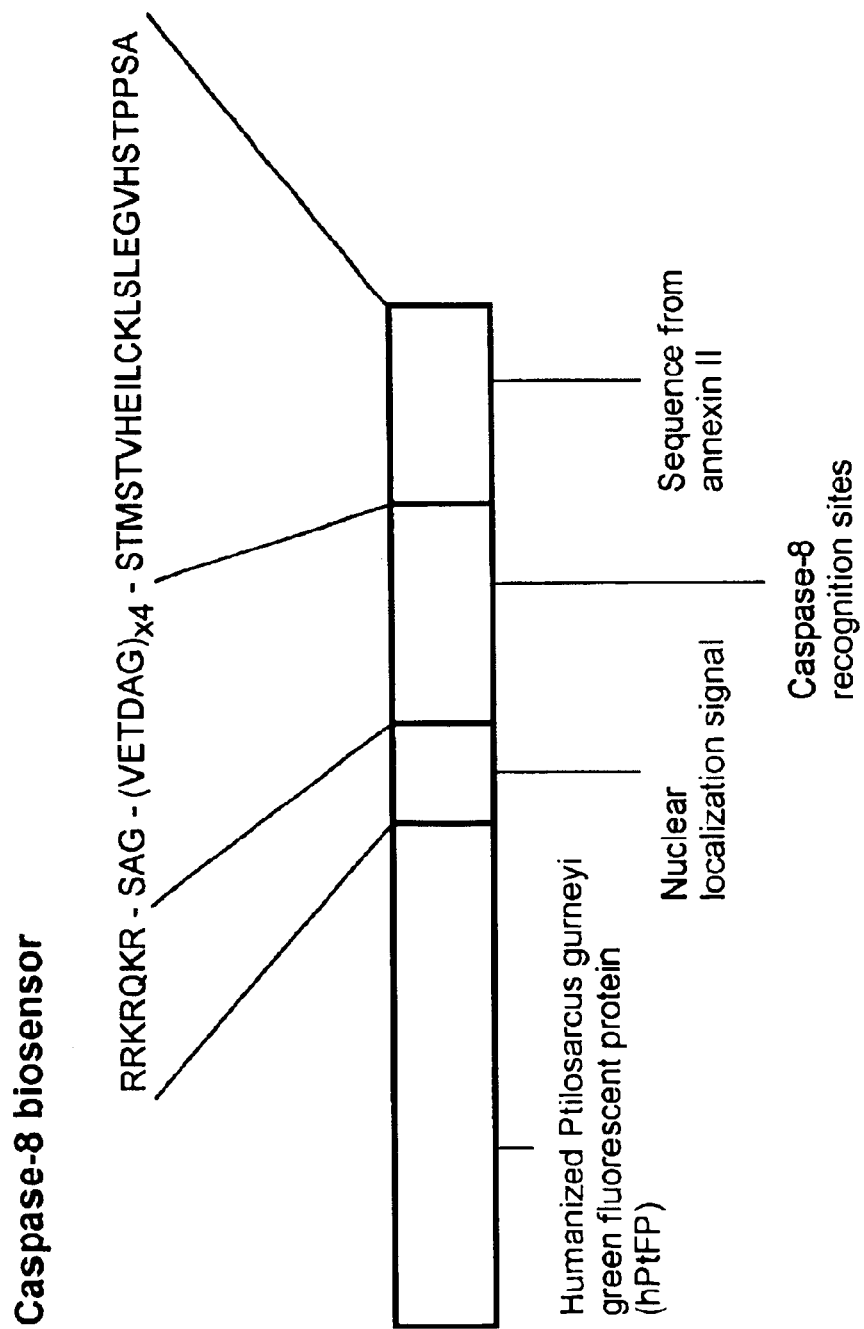

The organizations of the biosensors are shown in FIG. 7 (Caspase 3) and FIG. 8 (Caspase 8). Those persons skilled in the art will recognize that any one of a wide variety of protease recognition sites, reactant target sequences, polypeptide signals, and/or product target sequences can be used in various combinations in the protein biosensor of the present invention, by substituting the appropriate coding sequences into the multi-domain construct. Non-limiting examples of such alternative sequences are shown in FIGS. 7 and 8. Similarly, those skilled in the art will recognize that modifications, substitutions, and deletions can be made to the coding sequences and the amino acid sequences of each individual domain within the biosensor, while retaining the function of the domain. Such various combinations of domains and modifications, substitutions and deletions to individual domains are within the scope of the instant invention.

As used herein, the term "coding sequence" or a sequence which "encodes" a particular polypeptide sequence, refers to a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, such as for example, but is not limited to, cDNA from prokaryotic or eukaryotic mRNA, genomic DNA sequences from prokaryotic or eukaryotic DNA, and synthetic DNA sequences. A transcription termination sequence will usually be located 3' to the coding sequence.

As used herein, the term DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the DNA sequence of interest is capable of being transcribed and translated appropriately.

As used herein, the term "operatively linked" refers to an arrangement of elements wherein the components so described are configured so as to perform their usual function. Thus, control sequences operatively linked to a coding sequence are capable of effecting the expression of the coding sequence. The control sequences need not be contiguous with the coding sequence, so long as they function to direct expression thereof. Thus, for example, intervening untranslated yet transcribed sequences can be present between a promoter sequence and the coding sequence and the promoter sequence can still be considered "operatively linked" to the coding sequence.

Furthermore, a nucleic acid coding sequence is operatively linked to another nucleic acid coding sequence when the coding region for both nucleic acid molecules are capable of expression in the same reading frame. The nucleic acid sequences need not be contiguous, so long as they are capable of expression in the same reading frame. Thus, for example, intervening coding sequences, and the specified nucleic acid coding regions can still be considered "operatively linked".

The intervening coding sequences between the various domains of the biosensors can be of any length so long as the function of each domain is retained. Generally, this requires that the two dimensional and three-dimensional structure of the intervening protein sequence does not preclude the binding or interaction requirements of the domains of the biosensor, such as product or reactant targeting, binding of the protease of interest to the biosensor, fluorescence or luminescence of the detectable polypeptide signal, or binding of fluorescently labeled epitope-specific antibodies.

Within this application, unless otherwise noted, the techniques utilized may be found in any of several well-known references such as *Molecular Cloning: A Laboratory Manual* (Sambrook, et al. 1989, Cold Spring Harbor Laboratory Press), *Gene Expression Technology* (Methods in Enzymology, Vol. 185 edited by D. Goeddel, 1991, Academic Press, San Diego, Calif.), *"Guide to Protein Purification" in Methods in Enzymology* (M. P. Deutscher, ed., (1990) Academic Press, Inc.); *PCR Protocols: A Guide to Methods and Applications* (Innis, et al. 1990. Academic Press, San Diego, Calif.), *Culture of animal Cells: A Manual of Basic Technique,* 2nd Ed. (R. I. Freshney, 1987. Liss, Inc. New York, N.Y.) *Gene Transfer and Expression Protocols,* pp. 109–128, ed. E. J. Murray, The Human Press Inc. Clifton, N.J.), and the Ambion Catalog (Ambion, Austin, Tex.).

The biosensors of the present invention are constructed and used to transfect host cells using standard techniques in the molecular biological arts. Any number of such techniques, all of which are within the scope of this invention, can be used to generate protease biosensor-encoding DNA constructs and genetically transfected host cells expressing the biosensors. The biosensors disclosed in pending published patent application WO 0026408, entitled "A System For Cell Based Screening" provide examples of such biosensors; PCT/US99/25431 is made of record and incorporated by reference into this patent application. The non-limiting examples that follow demonstrate one such technique for constructing the biosensors of the invention. For example, by changing the protease recognition sequence of the sensors shown herein into the recognition sequence for other caspases or other intracellular proteases, such as for example calpain and cathepsins, new specific protease sensors can easily be generated. Other examples of green fluorescent protein-based biosensors include, but are not limited to, fluorescence resonance energy transfer (FRET) based, green fluorescent protein-based caspase sensor disclosed by J. Jones et al., *J. Biomol. Screen.*, Vol. 5 (5), pages 307–318 (October 2000), A. Miyawaki et al., *Nature,* Vol. 388 (6645), pages 882–887 (August 1997), and J. P. Waud et al., *J. Biochem.*, Vol. 357 (Pt. 3), pages 687–697 (August 2001).

In addition to the full length coding sequence hPtFP of the present invention as shown in Seq. ID No. 1 several truncation mutants are disclosed ranging from truncations at the 5' (amino) terminus to truncations at the 3' (carboxy) terminus. SEQ ID No. 2 shows the amino acid sequence of the full length hPtFP of the present invention. SEQ ID No. 3 shows a truncation mutant of the present invention wherein the truncation occurs at the 3' (carboxy) terminus, specifically, including amino acid sequence 1–224. SEQ ID No. 4 shows a truncation mutant of the present invention wherein the truncation occurs at the 5' (amino) terminus, specifically including amino acid sequence 10–229. FIG. 13 shows deletion mutants of the hPtFP of the present invention that were constructed. The fluorescent intensity upon visual inspection of each construct is shown in FIG. 13. The deletion mutants of the hPtFP of the present invention were constructed and transiently transfected into HeLa cells. The deletion mutants were created by employing PCR (polymerase chain reaction) technology, as known by those skilled in the art, and were sub-cloned into the expression vector M2 in which the expression in the mammalian systems is driven by the CMV (cytomegalovirus) promoter. All mutants and the full length hPtFP of this invention, expression constructs were designed to be identical in the non-coding region. All coding regions constructed for this comparison as shown in FIG. 13 retain M (methionine) and V (valine) as the first and second amino acids, respectively. The plasmids were then transfected into Hela cells and observed for fluorescence 24 hours after transfection as shown in FIG. 13. It will be appreciated by those skilled in the art that the truncation mutants of the present invention may be employed as fluorescent tags for monitoring the activities of its fusion partners using an image based approach as a biosensor.

FIG. 14 shows HeLa cells (CCL-2, ATCC, 10801, Manassas, Va., USA) transfected with with the hPtFP-Caspase-8 biosensor with FUGENE 6 reagent (Roche Molecular Biochemicals, Indianapolis, Ind., USA). Twenty four hours after transfection, the HeLa cells were treated with staurosporine (Sigma-Aldrich, St. Louis, Mo., USA), at 1 nM (nano molar) or 10 nM. Fluorescent signals from the cells were observed at the 6 hours and 24 hours, respectively, after addition of the staurosporine to the medium.

Whereas particular embodiments of this invention have been described herein for purposes of illustration, it will be evident to those persons skilled in the art that numerous variations of the details of the present invention may be made without departing from the invention as defined in the appended claims that follow the SEQUENCE LISTING.

SEQUENCE LISTING

<160> NUMBER OF SEQ ID NOS: 27

<210> SEQ ID NO 1
<211> LENGTH: 1482
<212> TYPE: DNA
<213> ORGANISM: Ptilosarcus gurneyi

<400> SEQUENCE: 1

```
aagcttgcca ccatggtgaa ccggaacgtg ctgaagaaca ccggcctgaa ggagatcatg        60
agcgccaagg ccagcgtgga gggcatcgtg aacaaccacg tgttcagcat ggagggcttc       120
ggcaagggca acgtgctgtt cggcaaccag ctgatgcaga tccgggtgac caagggcggc       180
cctctgccct tcgccttcga catcgtgagc atcgccttcc agtacggcaa ccggaccttc       240
accaagtatc ccgacgacat cgccgactac ttcgtgcaga gcttccctgc cggcttcttc       300
tacgagcgga acctgcggtt cgaggacggc gccatcgtgg acatccggag cgacatcagc       360
ctggaggacg acaagttcca ctacaaggtg gagtaccgcg gcaacggctt ccctagcaac       420
ggccctgtga tgcagaaggc catcctgggc atggagccca gcttcgaggt ggtgtacatg       480
aacagcggcg tgctggtggg cgaggtggac ctggtgtaca gctggagag cggcaactac       540 tacagctgcc acatgaagac cttctaccgg agcaagggcg gcgtgaagga gttccctgag       600
tacctattca tccaccaccg gctggagaag aactacgtgg aggagggcag cttcgtggag       660
cagcacgaga ccgccatcgc ccagctgacc accatcggca gcctctggg cagcctgcac       720 gagtgggtgt aaagcggccg caagcttgcc accatggtga accggaacgt gctgaagaac       780
accggcctga aggagatcat gagcgccaag gccagcgtgg agggcatcgt gaacaaccac       840
gtgttcagca tggagggctt cggcaagggc aacgtgctgt tcggcaacca gctgatgcag       900
atccgggtga ccaagggcgg ccctctgccc ttcgccttcg acatcgtgag catcgccttc       960
cagtacggca accggacctt caccaagtat cccgacgaca tcgccgacta cttcgtgcag      1020
agcttccctg ccggcttctt ctacgagcgg aacctgcggt tcgaggacgg cgccatcgtg      1080
gacatccgga gcgacatcag cctggaggac gacaagttcc actacaaggt ggagtaccgc      1140
ggcaacggct tccctagcaa cggccctgtg atgcagaagg ccatcctggg catggagccc      1200
agcttcgagg tggtgtacat gaacagcggc gtgctggtgg gcgaggtgga cctggtgtac      1260
agctggagag cgcaactac tacagctgc cacatgaaga ccttctaccg gagcaagggc      1320
ggcgtgaagg agttccctga gtacctattc atccaccacc ggctggagaa gaactacgtg      1380
```

-continued

```
gaggagggca gcttcgtgga gcagcacgag accgccatcg cccagctgac caccatcggc    1440
aagcctctgg gcagcctgca cgagtgggtg taaagcggcc gc                       1482
```

<210> SEQ ID NO 2
<211> LENGTH: 239
<212> TYPE: PRT
<213> ORGANISM: Ptilosarcus gurneyi

<400> SEQUENCE: 2

```
Met Val Asn Arg Asn Val Leu Lys Asn Thr Gly Leu Lys Glu Ile Met
1               5                   10                  15

Ser Ala Lys Ala Ser Val Glu Gly Ile Val Asn Asn His Val Phe Ser
                20                  25                  30

Met Glu Gly Phe Gly Lys Gly Asn Val Leu Phe Gly Asn Gln Leu Met
            35                  40                  45

Gln Ile Arg Val Thr Lys Gly Gly Pro Leu Pro Phe Ala Phe Asp Ile
        50                  55                  60

Val Ser Ile Ala Phe Gln Tyr Gly Asn Arg Thr Phe Thr Lys Tyr Pro
65                  70                  75                  80

Asp Asp Ile Ala Asp Tyr Phe Val Gln Ser Phe Pro Ala Gly Phe Phe
                85                  90                  95

Tyr Glu Arg Asn Leu Arg Phe Glu Asp Gly Ala Ile Val Asp Ile Arg
            100                 105                 110

Ser Asp Ile Ser Leu Glu Asp Asp Lys Phe His Tyr Lys Val Glu Tyr
        115                 120                 125

Arg Gly Asn Gly Phe Pro Ser Asn Gly Pro Val Met Gln Lys Ala Ile
    130                 135                 140

Leu Gly Met Glu Pro Ser Phe Glu Val Val Tyr Met Asn Ser Gly Val
145                 150                 155                 160

Leu Val Gly Glu Val Asp Leu Val Tyr Lys Leu Glu Ser Gly Asn Tyr
                165                 170                 175

Tyr Ser Cys His Met Lys Thr Phe Tyr Arg Ser Lys Gly Gly Val Lys
            180                 185                 190

Glu Phe Pro Glu Tyr His Phe Ile His His Arg Leu Glu Lys Thr Tyr
        195                 200                 205

Val Glu Glu Gly Ser Phe Val Glu Gln His Glu Thr Ala Ile Ala Gln
    210                 215                 220

Leu Thr Thr Ile Gly Lys Pro Leu Gly Ser Leu His Glu Trp Val
225                 230                 235
```

<210> SEQ ID NO 3
<211> LENGTH: 224
<212> TYPE: PRT
<213> ORGANISM: Ptilosarcus gurneyi

<400> SEQUENCE: 3

```
Met Val Asn Arg Asn Val Leu Lys Asn Thr Gly Leu Lys Glu Ile Met
1               5                   10                  15

Ser Ala Lys Ala Ser Val Glu Gly Ile Val Asn Asn His Val Phe Ser
                20                  25                  30

Met Glu Gly Phe Gly Lys Gly Asn Val Leu Phe Gly Asn Gln Leu Met
            35                  40                  45

Gln Ile Arg Val Thr Lys Gly Gly Pro Leu Pro Phe Ala Phe Asp Ile
        50                  55                  60

Val Ser Ile Ala Phe Gln Tyr Gly Asn Arg Thr Phe Thr Lys Tyr Pro
```

-continued

```
                 65                  70                  75                  80
Asp Asp Ile Ala Asp Tyr Phe Val Gln Ser Phe Pro Ala Gly Phe Phe
                 85                  90                  95

Tyr Glu Arg Asn Leu Arg Phe Glu Asp Gly Ala Ile Val Asp Ile Arg
                100                 105                 110

Ser Asp Ile Ser Leu Glu Asp Asp Lys Phe His Tyr Lys Val Glu Tyr
                115                 120                 125

Arg Gly Asn Gly Phe Pro Ser Asn Gly Pro Val Met Gln Lys Ala Ile
                130                 135                 140

Leu Gly Met Glu Pro Ser Phe Glu Val Val Tyr Met Asn Ser Gly Val
145                 150                 155                 160

Leu Val Gly Glu Val Asp Leu Val Tyr Lys Leu Glu Ser Gly Asn Tyr
                165                 170                 175

Tyr Ser Cys His Met Lys Thr Phe Tyr Arg Ser Lys Gly Gly Val Lys
                180                 185                 190

Glu Phe Pro Glu Tyr His Phe Ile His His Arg Leu Glu Lys Thr Tyr
                195                 200                 205

Val Glu Glu Gly Ser Phe Val Glu Gln His Glu Thr Ala Ile Ala Gln
                210                 215                 220

<210> SEQ ID NO 4
<211> LENGTH: 219
<212> TYPE: PRT
<213> ORGANISM: Ptilosarcus gurneyi

<400> SEQUENCE: 4

Gly Leu Lys Glu Ile Met Ser Ala Lys Ala Ser Val Glu Gly Ile Val
1                   5                  10                  15

Asn Asn His Val Phe Ser Met Glu Gly Phe Gly Lys Gly Asn Val Leu
                 20                  25                  30

Phe Gly Asn Gln Leu Met Gln Ile Arg Val Thr Lys Gly Gly Pro Leu
                 35                  40                  45

Pro Phe Ala Phe Asp Ile Val Ser Ile Ala Phe Gln Tyr Gly Asn Arg
                 50                  55                  60

Thr Phe Thr Lys Tyr Pro Asp Asp Ile Ala Asp Tyr Phe Val Gln Ser
65                  70                  75                  80

Phe Pro Ala Gly Phe Phe Tyr Glu Arg Asn Leu Arg Phe Glu Asp Gly
                 85                  90                  95

Ala Ile Val Asp Ile Arg Ser Asp Ile Ser Leu Glu Asp Asp Lys Phe
                100                 105                 110

His Tyr Lys Val Glu Tyr Arg Gly Asn Gly Phe Pro Ser Asn Gly Pro
                115                 120                 125

Val Met Gln Lys Ala Ile Leu Gly Met Glu Pro Ser Phe Glu Val Val
                130                 135                 140

Tyr Met Asn Ser Gly Val Leu Val Gly Glu Val Asp Leu Val Tyr Lys
145                 150                 155                 160

Leu Glu Ser Gly Asn Tyr Tyr Ser Cys His Met Lys Thr Phe Tyr Arg
                165                 170                 175

Ser Lys Gly Gly Val Lys Glu Phe Pro Glu Tyr His Phe Ile His His
                180                 185                 190

Arg Leu Glu Lys Thr Tyr Val Glu Glu Gly Ser Phe Val Glu Gln His
                195                 200                 205

Glu Thr Ala Ile Ala Gln Leu Thr Thr Ile Gly
                210                 215
```

<210> SEQ ID NO 5
<211> LENGTH: 238
<212> TYPE: PRT
<213> ORGANISM: Ptilosarcus gurneyi

<400> SEQUENCE: 5

```
Met Val Arg Asn Val Leu Lys Asn Thr Gly Leu Lys Glu Ile Met Ser
1               5                   10                  15

Ala Lys Ala Ser Val Glu Gly Ile Val Asn Asn His Val Phe Ser Met
            20                  25                  30

Glu Gly Phe Gly Lys Gly Asn Val Leu Phe Gly Asn Gln Leu Met Gln
        35                  40                  45

Ile Arg Val Thr Lys Gly Gly Pro Leu Pro Phe Ala Phe Asp Ile Val
50                  55                  60

Ser Ile Ala Phe Gln Tyr Gly Asn Arg Thr Phe Thr Lys Tyr Pro Asp
65                  70                  75                  80

Asp Ile Ala Asp Tyr Phe Val Gln Ser Phe Pro Ala Gly Phe Phe Tyr
                85                  90                  95

Glu Arg Asn Leu Arg Phe Glu Asp Gly Ala Ile Val Asp Ile Arg Ser
            100                 105                 110

Asp Ile Ser Leu Glu Asp Asp Lys Phe His Tyr Lys Val Glu Tyr Arg
        115                 120                 125

Gly Asn Gly Phe Pro Ser Asn Gly Pro Val Met Gln Lys Ala Ile Leu
    130                 135                 140

Gly Met Glu Pro Ser Phe Glu Val Val Tyr Met Asn Ser Gly Val Leu
145                 150                 155                 160

Val Gly Glu Val Asp Leu Val Tyr Lys Leu Glu Ser Gly Asn Tyr Tyr
                165                 170                 175

Ser Cys His Met Lys Thr Phe Tyr Arg Ser Lys Gly Gly Val Lys Glu
            180                 185                 190

Phe Pro Glu Tyr His Phe Ile His His Arg Leu Glu Lys Thr Tyr Val
        195                 200                 205

Glu Glu Gly Ser Phe Val Glu Gln His Glu Thr Ala Ile Ala Gln Leu
    210                 215                 220

Thr Thr Ile Gly Lys Pro Leu Gly Ser Leu His Glu Trp Val
225                 230                 235
```

<210> SEQ ID NO 6
<211> LENGTH: 237
<212> TYPE: PRT
<213> ORGANISM: Ptilosarcus gurneyi

<400> SEQUENCE: 6

```
Met Val Asn Val Leu Lys Asn Thr Gly Leu Lys Glu Ile Met Ser Ala
1               5                   10                  15

Lys Ala Ser Val Glu Gly Ile Val Asn Asn His Val Phe Ser Met Glu
            20                  25                  30

Gly Phe Gly Lys Gly Asn Val Leu Phe Gly Asn Gln Leu Met Gln Ile
        35                  40                  45

Arg Val Thr Lys Gly Gly Pro Leu Pro Phe Ala Phe Asp Ile Val Ser
    50                  55                  60

Ile Ala Phe Gln Tyr Gly Asn Arg Thr Phe Thr Lys Tyr Pro Asp Asp
65                  70                  75                  80

Ile Ala Asp Tyr Phe Val Gln Ser Phe Pro Ala Gly Phe Phe Tyr Glu
                85                  90                  95
```

```
Arg Asn Leu Arg Phe Glu Asp Gly Ala Ile Val Asp Ile Arg Ser Asp
            100                 105                 110
Ile Ser Leu Glu Asp Asp Lys Phe His Tyr Lys Val Glu Tyr Arg Gly
            115                 120                 125
Asn Gly Phe Pro Ser Asn Gly Pro Val Met Gln Lys Ala Ile Leu Gly
        130                 135                 140
Met Glu Pro Ser Phe Glu Val Val Tyr Met Asn Ser Gly Val Leu Val
145                 150                 155                 160
Gly Glu Val Asp Leu Val Tyr Lys Leu Glu Ser Gly Asn Tyr Tyr Ser
                165                 170                 175
Cys His Met Lys Thr Phe Tyr Arg Ser Lys Gly Val Lys Glu Phe
            180                 185                 190
Pro Glu Tyr His Phe Ile His His Arg Leu Glu Lys Thr Tyr Val Glu
            195                 200                 205
Glu Gly Ser Phe Val Glu Gln His Glu Thr Ala Ile Ala Gln Leu Thr
        210                 215                 220
Thr Ile Gly Lys Pro Leu Gly Ser Leu His Glu Trp Val
225                 230                 235
```

<210> SEQ ID NO 7
<211> LENGTH: 236
<212> TYPE: PRT
<213> ORGANISM: Ptilosarcus gurneyi

<400> SEQUENCE: 7

```
Met Val Val Leu Lys Asn Thr Gly Leu Lys Glu Ile Met Ser Ala Lys
1               5                   10                  15
Ala Ser Val Glu Gly Ile Val Asn Asn His Val Phe Ser Met Glu Gly
            20                  25                  30
Phe Gly Lys Gly Asn Val Leu Phe Gly Asn Gln Leu Met Gln Ile Arg
        35                  40                  45
Val Thr Lys Gly Gly Pro Leu Pro Phe Ala Phe Asp Ile Val Ser Ile
    50                  55                  60
Ala Phe Gln Tyr Gly Asn Arg Thr Phe Thr Lys Tyr Pro Asp Asp Ile
65                  70                  75                  80
Ala Asp Tyr Phe Val Gln Ser Phe Pro Ala Gly Phe Tyr Glu Arg
                85                  90                  95
Asn Leu Arg Phe Glu Asp Gly Ala Ile Val Asp Ile Arg Ser Asp Ile
            100                 105                 110
Ser Leu Glu Asp Asp Lys Phe His Tyr Lys Val Glu Tyr Arg Gly Asn
        115                 120                 125
Gly Phe Pro Ser Asn Gly Pro Val Met Gln Lys Ala Ile Leu Gly Met
    130                 135                 140
Glu Pro Ser Phe Glu Val Val Tyr Met Asn Ser Gly Val Leu Val Gly
145                 150                 155                 160
Glu Val Asp Leu Val Tyr Lys Leu Glu Ser Gly Asn Tyr Tyr Ser Cys
                165                 170                 175
His Met Lys Thr Phe Tyr Arg Ser Lys Gly Val Lys Glu Phe Pro
            180                 185                 190
Glu Tyr His Phe Ile His His Arg Leu Glu Lys Thr Tyr Val Glu Glu
        195                 200                 205
Gly Ser Phe Val Glu Gln His Glu Thr Ala Ile Ala Gln Leu Thr Thr
    210                 215                 220
Ile Gly Lys Pro Leu Gly Ser Leu His Glu Trp Val
225                 230                 235
```

<210> SEQ ID NO 8
<211> LENGTH: 235
<212> TYPE: PRT
<213> ORGANISM: Ptilosarcus gurneyi

<400> SEQUENCE: 8

```
Met Val Leu Lys Asn Thr Gly Leu Lys Glu Ile Met Ser Ala Lys Ala
1               5                   10                  15

Ser Val Glu Gly Ile Val Asn Asn His Val Phe Ser Met Glu Gly Phe
            20                  25                  30

Gly Lys Gly Asn Val Leu Phe Gly Asn Gln Leu Met Gln Ile Arg Val
        35                  40                  45

Thr Lys Gly Gly Pro Leu Pro Phe Ala Phe Asp Ile Val Ser Ile Ala
    50                  55                  60

Phe Gln Tyr Gly Asn Arg Thr Phe Thr Lys Tyr Pro Asp Asp Ile Ala
65                  70                  75                  80

Asp Tyr Phe Val Gln Ser Phe Pro Ala Gly Phe Phe Tyr Glu Arg Asn
                85                  90                  95

Leu Arg Phe Glu Asp Gly Ala Ile Val Asp Ile Arg Ser Asp Ile Ser
            100                 105                 110

Leu Glu Asp Asp Lys Phe His Tyr Lys Val Glu Tyr Arg Gly Asn Gly
        115                 120                 125

Phe Pro Ser Asn Gly Pro Val Met Gln Lys Ala Ile Leu Gly Met Glu
    130                 135                 140

Pro Ser Phe Glu Val Val Tyr Met Asn Ser Gly Val Leu Val Gly Glu
145                 150                 155                 160

Val Asp Leu Val Tyr Lys Leu Glu Ser Gly Asn Tyr Tyr Ser Cys His
                165                 170                 175

Met Lys Thr Phe Tyr Arg Ser Lys Gly Gly Val Lys Glu Phe Pro Glu
            180                 185                 190

Tyr His Phe Ile His His Arg Leu Glu Lys Thr Tyr Val Glu Glu Gly
        195                 200                 205

Ser Phe Val Glu Gln His Glu Thr Ala Ile Ala Gln Leu Thr Thr Ile
    210                 215                 220

Gly Lys Pro Leu Gly Ser Leu His Glu Trp Val
225                 230                 235
```

<210> SEQ ID NO 9
<211> LENGTH: 234
<212> TYPE: PRT
<213> ORGANISM: Ptilosarcus gurneyi

<400> SEQUENCE: 9

```
Met Val Lys Asn Thr Gly Leu Lys Glu Ile Met Ser Ala Lys Ala Ser
1               5                   10                  15

Val Glu Gly Ile Val Asn Asn His Val Phe Ser Met Glu Gly Phe Gly
            20                  25                  30

Lys Gly Asn Val Leu Phe Gly Asn Gln Leu Met Gln Ile Arg Val Thr
        35                  40                  45

Lys Gly Gly Pro Leu Pro Phe Ala Phe Asp Ile Val Ser Ile Ala Phe
    50                  55                  60

Gln Tyr Gly Asn Arg Thr Phe Thr Lys Tyr Pro Asp Asp Ile Ala Asp
65                  70                  75                  80

Tyr Phe Val Gln Ser Phe Pro Ala Gly Phe Phe Tyr Glu Arg Asn Leu
                85                  90                  95
```

```
Arg Phe Glu Asp Gly Ala Ile Val Asp Ile Arg Ser Asp Ile Ser Leu
            100                 105                 110

Glu Asp Asp Lys Phe His Tyr Lys Val Glu Tyr Arg Gly Asn Gly Phe
            115                 120                 125

Pro Ser Asn Gly Pro Val Met Gln Lys Ala Ile Leu Gly Met Glu Pro
            130                 135                 140

Ser Phe Glu Val Val Tyr Met Asn Ser Gly Val Leu Val Gly Glu Val
145                 150                 155                 160

Asp Leu Val Tyr Lys Leu Glu Ser Gly Asn Tyr Tyr Ser Cys His Met
            165                 170                 175

Lys Thr Phe Tyr Arg Ser Lys Gly Gly Val Lys Glu Phe Pro Glu Tyr
            180                 185                 190

His Phe Ile His His Arg Leu Glu Lys Thr Tyr Val Glu Glu Gly Ser
            195                 200                 205

Phe Val Glu Gln His Glu Thr Ala Ile Ala Gln Leu Thr Thr Ile Gly
            210                 215                 220

Lys Pro Leu Gly Ser Leu His Glu Trp Val
225                 230

<210> SEQ ID NO 10
<211> LENGTH: 233
<212> TYPE: PRT
<213> ORGANISM: Ptilosarcus gurneyi

<400> SEQUENCE: 10

Met Val Asn Thr Gly Leu Lys Glu Ile Met Ser Ala Lys Ala Ser Val
1               5                   10                  15

Glu Gly Ile Val Asn Asn His Val Phe Ser Met Glu Gly Phe Gly Lys
            20                  25                  30

Gly Asn Val Leu Phe Gly Asn Gln Leu Met Gln Ile Arg Val Thr Lys
            35                  40                  45

Gly Gly Pro Leu Pro Phe Ala Phe Asp Ile Val Ser Ile Ala Phe Gln
50                  55                  60

Tyr Gly Asn Arg Thr Phe Thr Lys Tyr Pro Asp Asp Ile Ala Asp Tyr
65                  70                  75                  80

Phe Val Gln Ser Phe Pro Ala Gly Phe Phe Tyr Glu Arg Asn Leu Arg
            85                  90                  95

Phe Glu Asp Gly Ala Ile Val Asp Ile Arg Ser Asp Ile Ser Leu Glu
            100                 105                 110

Asp Asp Lys Phe His Tyr Lys Val Glu Tyr Arg Gly Asn Gly Phe Pro
            115                 120                 125

Ser Asn Gly Pro Val Met Gln Lys Ala Ile Leu Gly Met Glu Pro Ser
            130                 135                 140

Phe Glu Val Val Tyr Met Asn Ser Gly Val Leu Val Gly Glu Val Asp
145                 150                 155                 160

Leu Val Tyr Lys Leu Glu Ser Gly Asn Tyr Tyr Ser Cys His Met Lys
            165                 170                 175

Thr Phe Tyr Arg Ser Lys Gly Gly Val Lys Glu Phe Pro Glu Tyr His
            180                 185                 190

Phe Ile His His Arg Leu Glu Lys Thr Tyr Val Glu Glu Gly Ser Phe
            195                 200                 205

Val Glu Gln His Glu Thr Ala Ile Ala Gln Leu Thr Thr Ile Gly Lys
            210                 215                 220

Pro Leu Gly Ser Leu His Glu Trp Val
```

```
                    225                 230

<210> SEQ ID NO 11
<211> LENGTH: 232
<212> TYPE: PRT
<213> ORGANISM: Ptilosarcus gurneyi

<400> SEQUENCE: 11

Met Val Thr Gly Leu Lys Glu Ile Met Ser Ala Lys Ala Ser Val Glu
1               5                   10                  15

Gly Ile Val Asn Asn His Val Phe Ser Met Glu Gly Phe Gly Lys Gly
            20                  25                  30

Asn Val Leu Phe Gly Asn Gln Leu Met Gln Ile Arg Val Thr Lys Gly
        35                  40                  45

Gly Pro Leu Pro Phe Ala Phe Asp Ile Val Ser Ile Ala Phe Gln Tyr
    50                  55                  60

Gly Asn Arg Thr Phe Thr Lys Tyr Pro Asp Asp Ile Ala Asp Tyr Phe
65                  70                  75                  80

Val Gln Ser Phe Pro Ala Gly Phe Phe Tyr Glu Arg Asn Leu Arg Phe
                85                  90                  95

Glu Asp Gly Ala Ile Val Asp Ile Arg Ser Asp Ile Ser Leu Glu Asp
            100                 105                 110

Asp Lys Phe His Tyr Lys Val Glu Tyr Arg Gly Asn Gly Phe Pro Ser
        115                 120                 125

Asn Gly Pro Val Met Gln Lys Ala Ile Leu Gly Met Glu Pro Ser Phe
    130                 135                 140

Glu Val Val Tyr Met Asn Ser Gly Val Leu Val Gly Glu Val Asp Leu
145                 150                 155                 160

Val Tyr Lys Leu Glu Ser Gly Asn Tyr Tyr Ser Cys His Met Lys Thr
                165                 170                 175

Phe Tyr Arg Ser Lys Gly Gly Val Lys Glu Phe Pro Glu Tyr His Phe
            180                 185                 190

Ile His His Arg Leu Glu Lys Thr Tyr Val Glu Glu Gly Ser Phe Val
        195                 200                 205

Glu Gln His Glu Thr Ala Ile Ala Gln Leu Thr Thr Ile Gly Lys Pro
    210                 215                 220

Leu Gly Ser Leu His Glu Trp Val
225                 230

<210> SEQ ID NO 12
<211> LENGTH: 231
<212> TYPE: PRT
<213> ORGANISM: Ptilosarcus gurneyi

<400> SEQUENCE: 12

Met Val Gly Leu Lys Glu Ile Met Ser Ala Lys Ala Ser Val Glu Gly
1               5                   10                  15

Ile Val Asn Asn His Val Phe Ser Met Glu Gly Phe Gly Lys Gly Asn
            20                  25                  30

Val Leu Phe Gly Asn Gln Leu Met Gln Ile Arg Val Thr Lys Gly Gly
        35                  40                  45

Pro Leu Pro Phe Ala Phe Asp Ile Val Ser Ile Ala Phe Gln Tyr Gly
    50                  55                  60

Asn Arg Thr Phe Thr Lys Tyr Pro Asp Asp Ile Ala Asp Tyr Phe Val
65                  70                  75                  80

Gln Ser Phe Pro Ala Gly Phe Phe Tyr Glu Arg Asn Leu Arg Phe Glu
```

```
                 85                  90                  95
Asp Gly Ala Ile Val Asp Ile Arg Ser Asp Ile Ser Leu Glu Asp Asp
            100                 105                 110
Lys Phe His Tyr Lys Val Glu Tyr Arg Gly Asn Gly Phe Pro Ser Asn
            115                 120                 125
Gly Pro Val Met Gln Lys Ala Ile Leu Gly Met Glu Pro Ser Phe Glu
            130                 135                 140
Val Val Tyr Met Asn Ser Gly Val Leu Val Gly Glu Val Asp Leu Val
145                 150                 155                 160
Tyr Lys Leu Glu Ser Gly Asn Tyr Tyr Ser Cys His Met Lys Thr Phe
                165                 170                 175
Tyr Arg Ser Lys Gly Val Lys Glu Phe Pro Glu Tyr His Phe Ile
            180                 185                 190
His His Arg Leu Glu Lys Thr Tyr Val Glu Glu Gly Ser Phe Val Glu
            195                 200                 205
Gln His Glu Thr Ala Ile Ala Gln Leu Thr Thr Ile Gly Lys Pro Leu
            210                 215                 220
Gly Ser Leu His Glu Trp Val
225                 230

<210> SEQ ID NO 13
<211> LENGTH: 224
<212> TYPE: PRT
<213> ORGANISM: Ptilosarcus gurneyi

<400> SEQUENCE: 13

Met Val Asn Arg Asn Val Leu Lys Asn Thr Gly Leu Lys Glu Ile Met
1               5                   10                  15
Ser Ala Lys Ala Ser Val Glu Gly Ile Val Asn Asn His Val Phe Ser
            20                  25                  30
Met Glu Gly Phe Gly Lys Gly Asn Val Leu Phe Gly Asn Gln Leu Met
            35                  40                  45
Gln Ile Arg Val Thr Lys Gly Gly Pro Leu Pro Phe Ala Phe Asp Ile
        50                  55                  60
Val Ser Ile Ala Phe Gln Tyr Gly Asn Arg Thr Phe Thr Lys Tyr Pro
65                  70                  75                  80
Asp Asp Ile Ala Asp Tyr Phe Val Gln Ser Phe Pro Ala Gly Phe Phe
                85                  90                  95
Tyr Glu Arg Asn Leu Arg Phe Glu Asp Gly Ala Ile Val Asp Ile Arg
            100                 105                 110
Ser Asp Ile Ser Leu Glu Asp Asp Lys Phe His Tyr Lys Val Glu Tyr
            115                 120                 125
Arg Gly Asn Gly Phe Pro Ser Asn Gly Pro Val Met Gln Lys Ala Ile
            130                 135                 140
Leu Gly Met Glu Pro Ser Phe Glu Val Val Tyr Met Asn Ser Gly Val
145                 150                 155                 160
Leu Val Gly Glu Val Asp Leu Val Tyr Lys Leu Glu Ser Gly Asn Tyr
                165                 170                 175
Tyr Ser Cys His Met Lys Thr Phe Tyr Arg Ser Lys Gly Val Lys
            180                 185                 190
Glu Phe Pro Glu Tyr His Phe Ile His His Arg Leu Glu Lys Thr Tyr
            195                 200                 205
Val Glu Glu Gly Ser Phe Val Glu Gln His Glu Thr Ala Ile Ala Gln
            210                 215                 220
```

<210> SEQ ID NO 14
<211> LENGTH: 225
<212> TYPE: PRT
<213> ORGANISM: Ptilosarcus gurneyi

<400> SEQUENCE: 14

```
Met Val Asn Arg Asn Val Leu Lys Asn Thr Gly Leu Lys Glu Ile Met
1               5                   10                  15

Ser Ala Lys Ala Ser Val Glu Gly Ile Val Asn Asn His Val Phe Ser
            20                  25                  30

Met Glu Gly Phe Gly Lys Gly Asn Val Leu Phe Gly Asn Gln Leu Met
        35                  40                  45

Gln Ile Arg Val Thr Lys Gly Gly Pro Leu Pro Phe Ala Phe Asp Ile
    50                  55                  60

Val Ser Ile Ala Phe Gln Tyr Gly Asn Arg Thr Phe Thr Lys Tyr Pro
65                  70                  75                  80

Asp Asp Ile Ala Asp Tyr Phe Val Gln Ser Phe Pro Ala Gly Phe Phe
                85                  90                  95

Tyr Glu Arg Asn Leu Arg Phe Glu Asp Gly Ala Ile Val Asp Ile Arg
            100                 105                 110

Ser Asp Ile Ser Leu Glu Asp Asp Lys Phe His Tyr Lys Val Glu Tyr
        115                 120                 125

Arg Gly Asn Gly Phe Pro Ser Asn Gly Pro Val Met Gln Lys Ala Ile
    130                 135                 140

Leu Gly Met Glu Pro Ser Phe Glu Val Val Tyr Met Asn Ser Gly Val
145                 150                 155                 160

Leu Val Gly Glu Val Asp Leu Val Tyr Lys Leu Glu Ser Gly Asn Tyr
                165                 170                 175

Tyr Ser Cys His Met Lys Thr Phe Tyr Arg Ser Lys Gly Gly Val Lys
            180                 185                 190

Glu Phe Pro Glu Tyr His Phe Ile His His Arg Leu Glu Lys Thr Tyr
        195                 200                 205

Val Glu Glu Gly Ser Phe Val Glu Gln His Glu Thr Ala Ile Ala Gln
    210                 215                 220

Leu
225
```

<210> SEQ ID NO 15
<211> LENGTH: 226
<212> TYPE: PRT
<213> ORGANISM: Ptilosarcus gurneyi

<400> SEQUENCE: 15

```
Met Val Asn Arg Asn Val Leu Lys Asn Thr Gly Leu Lys Glu Ile Met
1               5                   10                  15

Ser Ala Lys Ala Ser Val Glu Gly Ile Val Asn Asn His Val Phe Ser
            20                  25                  30

Met Glu Gly Phe Gly Lys Gly Asn Val Leu Phe Gly Asn Gln Leu Met
        35                  40                  45

Gln Ile Arg Val Thr Lys Gly Gly Pro Leu Pro Phe Ala Phe Asp Ile
    50                  55                  60

Val Ser Ile Ala Phe Gln Tyr Gly Asn Arg Thr Phe Thr Lys Tyr Pro
65                  70                  75                  80

Asp Asp Ile Ala Asp Tyr Phe Val Gln Ser Phe Pro Ala Gly Phe Phe
                85                  90                  95
```

```
Tyr Glu Arg Asn Leu Arg Phe Glu Asp Gly Ala Ile Val Asp Ile Arg
            100                 105                 110

Ser Asp Ile Ser Leu Glu Asp Asp Lys Phe His Tyr Lys Val Glu Tyr
        115                 120                 125

Arg Gly Asn Gly Phe Pro Ser Asn Gly Pro Val Met Gln Lys Ala Ile
    130                 135                 140

Leu Gly Met Glu Pro Ser Phe Glu Val Val Tyr Met Asn Ser Gly Val
145                 150                 155                 160

Leu Val Gly Glu Val Asp Leu Val Tyr Lys Leu Glu Ser Gly Asn Tyr
                165                 170                 175

Tyr Ser Cys His Met Lys Thr Phe Tyr Arg Ser Lys Gly Gly Val Lys
            180                 185                 190

Glu Phe Pro Glu Tyr His Phe Ile His His Arg Leu Glu Lys Thr Tyr
        195                 200                 205

Val Glu Glu Gly Ser Phe Val Glu Gln His Glu Thr Ala Ile Ala Gln
    210                 215                 220

Leu Thr
225

<210> SEQ ID NO 16
<211> LENGTH: 227
<212> TYPE: PRT
<213> ORGANISM: Ptilosarcus gurneyi

<400> SEQUENCE: 16

Met Val Asn Arg Asn Val Leu Lys Asn Thr Gly Leu Lys Glu Ile Met
1               5                   10                  15

Ser Ala Lys Ala Ser Val Glu Gly Ile Val Asn Asn His Val Phe Ser
            20                  25                  30

Met Glu Gly Phe Gly Lys Gly Asn Val Leu Phe Gly Asn Gln Leu Met
        35                  40                  45

Gln Ile Arg Val Thr Lys Gly Gly Pro Leu Pro Phe Ala Phe Asp Ile
    50                  55                  60

Val Ser Ile Ala Phe Gln Tyr Gly Asn Arg Thr Phe Thr Lys Tyr Pro
65                  70                  75                  80

Asp Asp Ile Ala Asp Tyr Phe Val Gln Ser Phe Pro Ala Gly Phe Phe
                85                  90                  95

Tyr Glu Arg Asn Leu Arg Phe Glu Asp Gly Ala Ile Val Asp Ile Arg
            100                 105                 110

Ser Asp Ile Ser Leu Glu Asp Asp Lys Phe His Tyr Lys Val Glu Tyr
        115                 120                 125

Arg Gly Asn Gly Phe Pro Ser Asn Gly Pro Val Met Gln Lys Ala Ile
    130                 135                 140

Leu Gly Met Glu Pro Ser Phe Glu Val Val Tyr Met Asn Ser Gly Val
145                 150                 155                 160

Leu Val Gly Glu Val Asp Leu Val Tyr Lys Leu Glu Ser Gly Asn Tyr
                165                 170                 175

Tyr Ser Cys His Met Lys Thr Phe Tyr Arg Ser Lys Gly Gly Val Lys
            180                 185                 190

Glu Phe Pro Glu Tyr His Phe Ile His His Arg Leu Glu Lys Thr Tyr
        195                 200                 205

Val Glu Glu Gly Ser Phe Val Glu Gln His Glu Thr Ala Ile Ala Gln
    210                 215                 220

Leu Thr Thr
225
```

<210> SEQ ID NO 17
<211> LENGTH: 228
<212> TYPE: PRT
<213> ORGANISM: Ptilosarcus gurneyi

<400> SEQUENCE: 17

```
Met Val Asn Arg Asn Val Leu Lys Asn Thr Gly Leu Lys Glu Ile Met
1               5                   10                  15

Ser Ala Lys Ala Ser Val Glu Gly Ile Val Asn Asn His Val Phe Ser
            20                  25                  30

Met Glu Gly Phe Gly Lys Gly Asn Val Leu Phe Gly Asn Gln Leu Met
        35                  40                  45

Gln Ile Arg Val Thr Lys Gly Gly Pro Leu Pro Phe Ala Phe Asp Ile
    50                  55                  60

Val Ser Ile Ala Phe Gln Tyr Gly Asn Arg Thr Phe Thr Lys Tyr Pro
65                  70                  75                  80

Asp Asp Ile Ala Asp Tyr Phe Val Gln Ser Phe Pro Ala Gly Phe Phe
                85                  90                  95

Tyr Glu Arg Asn Leu Arg Phe Glu Asp Gly Ala Ile Val Asp Ile Arg
            100                 105                 110

Ser Asp Ile Ser Leu Glu Asp Asp Lys Phe His Tyr Lys Val Glu Tyr
        115                 120                 125

Arg Gly Asn Gly Phe Pro Ser Asn Gly Pro Val Met Gln Lys Ala Ile
    130                 135                 140

Leu Gly Met Glu Pro Ser Phe Glu Val Val Tyr Met Asn Ser Gly Val
145                 150                 155                 160

Leu Val Gly Glu Val Asp Leu Val Tyr Lys Leu Glu Ser Gly Asn Tyr
                165                 170                 175

Tyr Ser Cys His Met Lys Thr Phe Tyr Arg Ser Lys Gly Gly Val Lys
            180                 185                 190

Glu Phe Pro Glu Tyr His Phe Ile His His Arg Leu Glu Lys Thr Tyr
        195                 200                 205

Val Glu Glu Gly Ser Phe Val Glu Gln His Glu Thr Ala Ile Ala Gln
    210                 215                 220

Leu Thr Thr Ile
225
```

<210> SEQ ID NO 18
<211> LENGTH: 229
<212> TYPE: PRT
<213> ORGANISM: Ptilosarcus gurneyi

<400> SEQUENCE: 18

```
Met Val Asn Arg Asn Val Leu Lys Asn Thr Gly Leu Lys Glu Ile Met
1               5                   10                  15

Ser Ala Lys Ala Ser Val Glu Gly Ile Val Asn Asn His Val Phe Ser
            20                  25                  30

Met Glu Gly Phe Gly Lys Gly Asn Val Leu Phe Gly Asn Gln Leu Met
        35                  40                  45

Gln Ile Arg Val Thr Lys Gly Gly Pro Leu Pro Phe Ala Phe Asp Ile
    50                  55                  60

Val Ser Ile Ala Phe Gln Tyr Gly Asn Arg Thr Phe Thr Lys Tyr Pro
65                  70                  75                  80

Asp Asp Ile Ala Asp Tyr Phe Val Gln Ser Phe Pro Ala Gly Phe Phe
                85                  90                  95
```

-continued

Tyr Glu Arg Asn Leu Arg Phe Glu Asp Gly Ala Ile Val Asp Ile Arg
                100                 105                 110

Ser Asp Ile Ser Leu Glu Asp Asp Lys Phe His Tyr Lys Val Glu Tyr
            115                 120                 125

Arg Gly Asn Gly Phe Pro Ser Asn Gly Pro Val Met Gln Lys Ala Ile
        130                 135                 140

Leu Gly Met Glu Pro Ser Phe Glu Val Val Tyr Met Asn Ser Gly Val
145                 150                 155                 160

Leu Val Gly Glu Val Asp Leu Val Tyr Lys Leu Glu Ser Gly Asn Tyr
                165                 170                 175

Tyr Ser Cys His Met Lys Thr Phe Tyr Arg Ser Lys Gly Gly Val Lys
            180                 185                 190

Glu Phe Pro Glu Tyr His Phe Ile His His Arg Leu Glu Lys Thr Tyr
        195                 200                 205

Val Glu Glu Gly Ser Phe Val Glu Gln His Glu Thr Ala Ile Ala Gln
    210                 215                 220

Leu Thr Thr Ile Gly
225

<210> SEQ ID NO 19
<211> LENGTH: 230
<212> TYPE: PRT
<213> ORGANISM: Ptilosarcus gurneyi

<400> SEQUENCE: 19

Met Val Asn Arg Asn Val Leu Lys Asn Thr Gly Leu Lys Glu Ile Met
1               5                   10                  15

Ser Ala Lys Ala Ser Val Glu Gly Ile Val Asn Asn His Val Phe Ser
            20                  25                  30

Met Glu Gly Phe Gly Lys Gly Asn Val Leu Phe Gly Asn Gln Leu Met
        35                  40                  45

Gln Ile Arg Val Thr Lys Gly Gly Pro Leu Pro Phe Ala Phe Asp Ile
    50                  55                  60

Val Ser Ile Ala Phe Gln Tyr Gly Asn Arg Thr Phe Thr Lys Tyr Pro
65                  70                  75                  80

Asp Asp Ile Ala Asp Tyr Phe Val Gln Ser Phe Pro Ala Gly Phe Phe
                85                  90                  95

Tyr Glu Arg Asn Leu Arg Phe Glu Asp Gly Ala Ile Val Asp Ile Arg
                100                 105                 110

Ser Asp Ile Ser Leu Glu Asp Asp Lys Phe His Tyr Lys Val Glu Tyr
            115                 120                 125

Arg Gly Asn Gly Phe Pro Ser Asn Gly Pro Val Met Gln Lys Ala Ile
        130                 135                 140

Leu Gly Met Glu Pro Ser Phe Glu Val Val Tyr Met Asn Ser Gly Val
145                 150                 155                 160

Leu Val Gly Glu Val Asp Leu Val Tyr Lys Leu Glu Ser Gly Asn Tyr
                165                 170                 175

Tyr Ser Cys His Met Lys Thr Phe Tyr Arg Ser Lys Gly Gly Val Lys
            180                 185                 190

Glu Phe Pro Glu Tyr His Phe Ile His His Arg Leu Glu Lys Thr Tyr
        195                 200                 205

Val Glu Glu Gly Ser Phe Val Glu Gln His Glu Thr Ala Ile Ala Gln
    210                 215                 220

Leu Thr Thr Ile Gly Lys

-continued

```
225                 230

<210> SEQ ID NO 20
<211> LENGTH: 231
<212> TYPE: PRT
<213> ORGANISM: Ptilosarcus gurneyi

<400> SEQUENCE: 20

Met Val Asn Arg Asn Val Leu Lys Asn Thr Gly Leu Lys Glu Ile Met
1               5                   10                  15

Ser Ala Lys Ala Ser Val Glu Gly Ile Val Asn Asn His Val Phe Ser
            20                  25                  30

Met Glu Gly Phe Gly Lys Gly Asn Val Leu Phe Gly Asn Gln Leu Met
        35                  40                  45

Gln Ile Arg Val Thr Lys Gly Gly Pro Leu Pro Phe Ala Phe Asp Ile
    50                  55                  60

Val Ser Ile Ala Phe Gln Tyr Gly Asn Arg Thr Phe Thr Lys Tyr Pro
65                  70                  75                  80

Asp Asp Ile Ala Asp Tyr Phe Val Gln Ser Phe Pro Ala Gly Phe Phe
                85                  90                  95

Tyr Glu Arg Asn Leu Arg Phe Glu Asp Gly Ala Ile Val Asp Ile Arg
            100                 105                 110

Ser Asp Ile Ser Leu Glu Asp Asp Lys Phe His Tyr Lys Val Glu Tyr
        115                 120                 125

Arg Gly Asn Gly Phe Pro Ser Asn Gly Pro Val Met Gln Lys Ala Ile
    130                 135                 140

Leu Gly Met Glu Pro Ser Phe Glu Val Val Tyr Met Asn Ser Gly Val
145                 150                 155                 160

Leu Val Gly Glu Val Asp Leu Val Tyr Lys Leu Glu Ser Gly Asn Tyr
                165                 170                 175

Tyr Ser Cys His Met Lys Thr Phe Tyr Arg Ser Lys Gly Gly Val Lys
            180                 185                 190

Glu Phe Pro Glu Tyr His Phe Ile His His Arg Leu Glu Lys Thr Tyr
        195                 200                 205

Val Glu Glu Gly Ser Phe Val Glu Gln His Glu Thr Ala Ile Ala Gln
    210                 215                 220

Leu Thr Thr Ile Gly Lys Pro
225                 230

<210> SEQ ID NO 21
<211> LENGTH: 232
<212> TYPE: PRT
<213> ORGANISM: Ptilosarcus gurneyi

<400> SEQUENCE: 21

Met Val Asn Arg Asn Val Leu Lys Asn Thr Gly Leu Lys Glu Ile Met
1               5                   10                  15

Ser Ala Lys Ala Ser Val Glu Gly Ile Val Asn Asn His Val Phe Ser
            20                  25                  30

Met Glu Gly Phe Gly Lys Gly Asn Val Leu Phe Gly Asn Gln Leu Met
        35                  40                  45

Gln Ile Arg Val Thr Lys Gly Gly Pro Leu Pro Phe Ala Phe Asp Ile
    50                  55                  60

Val Ser Ile Ala Phe Gln Tyr Gly Asn Arg Thr Phe Thr Lys Tyr Pro
65                  70                  75                  80

Asp Asp Ile Ala Asp Tyr Phe Val Gln Ser Phe Pro Ala Gly Phe Phe
```

-continued

```
                  85                  90                  95
Tyr Glu Arg Asn Leu Arg Phe Glu Asp Gly Ala Ile Val Asp Ile Arg
            100                 105                 110
Ser Asp Ile Ser Leu Glu Asp Asp Lys Phe His Tyr Lys Val Glu Tyr
            115                 120                 125
Arg Gly Asn Gly Phe Pro Ser Asn Gly Pro Val Met Gln Lys Ala Ile
            130                 135                 140
Leu Gly Met Glu Pro Ser Phe Glu Val Val Tyr Met Asn Ser Gly Val
145                 150                 155                 160
Leu Val Gly Glu Val Asp Leu Val Tyr Lys Leu Glu Ser Gly Asn Tyr
                165                 170                 175
Tyr Ser Cys His Met Lys Thr Phe Tyr Arg Ser Lys Gly Gly Val Lys
                180                 185                 190
Glu Phe Pro Glu Tyr His Phe Ile His His Arg Leu Glu Lys Thr Tyr
            195                 200                 205
Val Glu Glu Gly Ser Phe Val Glu Gln His Glu Thr Ala Ile Ala Gln
            210                 215                 220
Leu Thr Thr Ile Gly Lys Pro Leu
225                 230

<210> SEQ ID NO 22
<211> LENGTH: 233
<212> TYPE: PRT
<213> ORGANISM: Ptilosarcus gurneyi

<400> SEQUENCE: 22

Met Val Asn Arg Asn Val Leu Lys Asn Thr Gly Leu Lys Glu Ile Met
1               5                   10                  15
Ser Ala Lys Ala Ser Val Glu Gly Ile Val Asn Asn His Val Phe Ser
                20                  25                  30
Met Glu Gly Phe Gly Lys Gly Asn Val Leu Phe Gly Asn Gln Leu Met
            35                  40                  45
Gln Ile Arg Val Thr Lys Gly Gly Pro Leu Pro Phe Ala Phe Asp Ile
        50                  55                  60
Val Ser Ile Ala Phe Gln Tyr Gly Asn Arg Thr Phe Thr Lys Tyr Pro
65                  70                  75                  80
Asp Asp Ile Ala Asp Tyr Phe Val Gln Ser Phe Pro Ala Gly Phe Phe
                85                  90                  95
Tyr Glu Arg Asn Leu Arg Phe Glu Asp Gly Ala Ile Val Asp Ile Arg
            100                 105                 110
Ser Asp Ile Ser Leu Glu Asp Asp Lys Phe His Tyr Lys Val Glu Tyr
            115                 120                 125
Arg Gly Asn Gly Phe Pro Ser Asn Gly Pro Val Met Gln Lys Ala Ile
            130                 135                 140
Leu Gly Met Glu Pro Ser Phe Glu Val Val Tyr Met Asn Ser Gly Val
145                 150                 155                 160
Leu Val Gly Glu Val Asp Leu Val Tyr Lys Leu Glu Ser Gly Asn Tyr
                165                 170                 175
Tyr Ser Cys His Met Lys Thr Phe Tyr Arg Ser Lys Gly Gly Val Lys
                180                 185                 190
Glu Phe Pro Glu Tyr His Phe Ile His His Arg Leu Glu Lys Thr Tyr
            195                 200                 205
Val Glu Glu Gly Ser Phe Val Glu Gln His Glu Thr Ala Ile Ala Gln
            210                 215                 220
```

```
Leu Thr Thr Ile Gly Lys Pro Leu Gly
225                 230
```

<210> SEQ ID NO 23
<211> LENGTH: 234
<212> TYPE: PRT
<213> ORGANISM: Ptilosarcus gurneyi

<400> SEQUENCE: 23

```
Met Val Asn Arg Asn Val Leu Lys Asn Thr Gly Leu Lys Glu Ile Met
1               5                   10                  15

Ser Ala Lys Ala Ser Val Glu Gly Ile Val Asn Asn His Val Phe Ser
            20                  25                  30

Met Glu Gly Phe Gly Lys Gly Asn Val Leu Phe Gly Asn Gln Leu Met
        35                  40                  45

Gln Ile Arg Val Thr Lys Gly Gly Pro Leu Pro Phe Ala Phe Asp Ile
    50                  55                  60

Val Ser Ile Ala Phe Gln Tyr Gly Asn Arg Thr Phe Thr Lys Tyr Pro
65                  70                  75                  80

Asp Asp Ile Ala Asp Tyr Phe Val Gln Ser Phe Pro Ala Gly Phe Phe
                85                  90                  95

Tyr Glu Arg Asn Leu Arg Phe Glu Asp Gly Ala Ile Val Asp Ile Arg
            100                 105                 110

Ser Asp Ile Ser Leu Glu Asp Asp Lys Phe His Tyr Lys Val Glu Tyr
        115                 120                 125

Arg Gly Asn Gly Phe Pro Ser Asn Gly Pro Val Met Gln Lys Ala Ile
    130                 135                 140

Leu Gly Met Glu Pro Ser Phe Glu Val Val Tyr Met Asn Ser Gly Val
145                 150                 155                 160

Leu Val Gly Glu Val Asp Leu Val Tyr Lys Leu Glu Ser Gly Asn Tyr
                165                 170                 175

Tyr Ser Cys His Met Lys Thr Phe Tyr Arg Ser Lys Gly Gly Val Lys
            180                 185                 190

Glu Phe Pro Glu Tyr His Phe Ile His His Arg Leu Glu Lys Thr Tyr
        195                 200                 205

Val Glu Glu Gly Ser Phe Val Glu Gln His Glu Thr Ala Ile Ala Gln
    210                 215                 220

Leu Thr Thr Ile Gly Lys Pro Leu Gly Ser
225                 230
```

<210> SEQ ID NO 24
<211> LENGTH: 235
<212> TYPE: PRT
<213> ORGANISM: Ptilosarcus gurneyi

<400> SEQUENCE: 24

```
Met Val Asn Arg Asn Val Leu Lys Asn Thr Gly Leu Lys Glu Ile Met
1               5                   10                  15

Ser Ala Lys Ala Ser Val Glu Gly Ile Val Asn Asn His Val Phe Ser
            20                  25                  30

Met Glu Gly Phe Gly Lys Gly Asn Val Leu Phe Gly Asn Gln Leu Met
        35                  40                  45

Gln Ile Arg Val Thr Lys Gly Gly Pro Leu Pro Phe Ala Phe Asp Ile
    50                  55                  60

Val Ser Ile Ala Phe Gln Tyr Gly Asn Arg Thr Phe Thr Lys Tyr Pro
65                  70                  75                  80
```

```
Asp Asp Ile Ala Asp Tyr Phe Val Gln Ser Phe Pro Ala Gly Phe Phe
                85                  90                  95

Tyr Glu Arg Asn Leu Arg Phe Glu Asp Gly Ala Ile Val Asp Ile Arg
                100                 105                 110

Ser Asp Ile Ser Leu Glu Asp Asp Lys Phe His Tyr Lys Val Glu Tyr
                115                 120                 125

Arg Gly Asn Gly Phe Pro Ser Asn Gly Pro Val Met Gln Lys Ala Ile
                130                 135                 140

Leu Gly Met Glu Pro Ser Phe Glu Val Val Tyr Met Asn Ser Gly Val
145                 150                 155                 160

Leu Val Gly Glu Val Asp Leu Val Tyr Lys Leu Glu Ser Gly Asn Tyr
                165                 170                 175

Tyr Ser Cys His Met Lys Thr Phe Tyr Arg Ser Lys Gly Gly Val Lys
                180                 185                 190

Glu Phe Pro Glu Tyr His Phe Ile His His Arg Leu Glu Lys Thr Tyr
                195                 200                 205

Val Glu Glu Gly Ser Phe Val Glu Gln His Glu Thr Ala Ile Ala Gln
                210                 215                 220

Leu Thr Thr Ile Gly Lys Pro Leu Gly Ser Leu
225                 230                 235

<210> SEQ ID NO 25
<211> LENGTH: 236
<212> TYPE: PRT
<213> ORGANISM: Ptilosarcus gurneyi

<400> SEQUENCE: 25

Met Val Asn Arg Asn Val Leu Lys Asn Thr Gly Leu Lys Glu Ile Met
1               5                   10                  15

Ser Ala Lys Ala Ser Val Glu Gly Ile Val Asn Asn His Val Phe Ser
                20                  25                  30

Met Glu Gly Phe Gly Lys Gly Asn Val Leu Phe Gly Asn Gln Leu Met
                35                  40                  45

Gln Ile Arg Val Thr Lys Gly Gly Pro Leu Pro Phe Ala Phe Asp Ile
    50                  55                  60

Val Ser Ile Ala Phe Gln Tyr Gly Asn Arg Thr Phe Thr Lys Tyr Pro
65                  70                  75                  80

Asp Asp Ile Ala Asp Tyr Phe Val Gln Ser Phe Pro Ala Gly Phe Phe
                85                  90                  95

Tyr Glu Arg Asn Leu Arg Phe Glu Asp Gly Ala Ile Val Asp Ile Arg
                100                 105                 110

Ser Asp Ile Ser Leu Glu Asp Asp Lys Phe His Tyr Lys Val Glu Tyr
                115                 120                 125

Arg Gly Asn Gly Phe Pro Ser Asn Gly Pro Val Met Gln Lys Ala Ile
                130                 135                 140

Leu Gly Met Glu Pro Ser Phe Glu Val Val Tyr Met Asn Ser Gly Val
145                 150                 155                 160

Leu Val Gly Glu Val Asp Leu Val Tyr Lys Leu Glu Ser Gly Asn Tyr
                165                 170                 175

Tyr Ser Cys His Met Lys Thr Phe Tyr Arg Ser Lys Gly Gly Val Lys
                180                 185                 190

Glu Phe Pro Glu Tyr His Phe Ile His His Arg Leu Glu Lys Thr Tyr
                195                 200                 205

Val Glu Glu Gly Ser Phe Val Glu Gln His Glu Thr Ala Ile Ala Gln
                210                 215                 220
```

Leu Thr Thr Ile Gly Lys Pro Leu Gly Ser Leu His
225                 230                 235

<210> SEQ ID NO 26
<211> LENGTH: 237
<212> TYPE: PRT
<213> ORGANISM: Ptilosarcus gurneyi

<400> SEQUENCE: 26

Met Val Asn Arg Asn Val Leu Lys Asn Thr Gly Leu Lys Glu Ile Met
1               5                   10                  15

Ser Ala Lys Ala Ser Val Glu Gly Ile Val Asn Asn His Val Phe Ser
                20                  25                  30

Met Glu Gly Phe Gly Lys Gly Asn Val Leu Phe Gly Asn Gln Leu Met
            35                  40                  45

Gln Ile Arg Val Thr Lys Gly Gly Pro Leu Pro Phe Ala Phe Asp Ile
        50                  55                  60

Val Ser Ile Ala Phe Gln Tyr Gly Asn Arg Thr Phe Thr Lys Tyr Pro
65                  70                  75                  80

Asp Asp Ile Ala Asp Tyr Phe Val Gln Ser Phe Pro Ala Gly Phe Phe
                85                  90                  95

Tyr Glu Arg Asn Leu Arg Phe Glu Asp Gly Ala Ile Val Asp Ile Arg
            100                 105                 110

Ser Asp Ile Ser Leu Glu Asp Asp Lys Phe His Tyr Lys Val Glu Tyr
        115                 120                 125

Arg Gly Asn Gly Phe Pro Ser Asn Gly Pro Val Met Gln Lys Ala Ile
    130                 135                 140

Leu Gly Met Glu Pro Ser Phe Glu Val Val Tyr Met Asn Ser Gly Val
145                 150                 155                 160

Leu Val Gly Glu Val Asp Leu Val Tyr Lys Leu Glu Ser Gly Asn Tyr
                165                 170                 175

Tyr Ser Cys His Met Lys Thr Phe Tyr Arg Ser Lys Gly Gly Val Lys
            180                 185                 190

Glu Phe Pro Glu Tyr His Phe Ile His His Arg Leu Glu Lys Thr Tyr
        195                 200                 205

Val Glu Glu Gly Ser Phe Val Glu Gln His Glu Thr Ala Ile Ala Gln
    210                 215                 220

Leu Thr Thr Ile Gly Lys Pro Leu Gly Ser Leu His Glu
225                 230                 235

<210> SEQ ID NO 27
<211> LENGTH: 238
<212> TYPE: PRT
<213> ORGANISM: Ptilosarcus gurneyi

<400> SEQUENCE: 27

Met Val Asn Arg Asn Val Leu Lys Asn Thr Gly Leu Lys Glu Ile Met
1               5                   10                  15

Ser Ala Lys Ala Ser Val Glu Gly Ile Val Asn Asn His Val Phe Ser
                20                  25                  30

Met Glu Gly Phe Gly Lys Gly Asn Val Leu Phe Gly Asn Gln Leu Met
            35                  40                  45

Gln Ile Arg Val Thr Lys Gly Gly Pro Leu Pro Phe Ala Phe Asp Ile
        50                  55                  60

Val Ser Ile Ala Phe Gln Tyr Gly Asn Arg Thr Phe Thr Lys Tyr Pro
65                  70                  75                  80

-continued

```
Asp Asp Ile Ala Asp Tyr Phe Val Gln Ser Phe Pro Ala Gly Phe Phe
            85                  90                  95

Tyr Glu Arg Asn Leu Arg Phe Glu Asp Gly Ala Ile Val Asp Ile Arg
            100                 105                 110

Ser Asp Ile Ser Leu Glu Asp Asp Lys Phe His Tyr Lys Val Glu Tyr
            115                 120                 125

Arg Gly Asn Gly Phe Pro Ser Asn Gly Pro Val Met Gln Lys Ala Ile
            130                 135                 140

Leu Gly Met Glu Pro Ser Phe Glu Val Val Tyr Met Asn Ser Gly Val
145                 150                 155                 160

Leu Val Gly Glu Val Asp Leu Val Tyr Lys Leu Glu Ser Gly Asn Tyr
                165                 170                 175

Tyr Ser Cys His Met Lys Thr Phe Tyr Arg Ser Lys Gly Gly Val Lys
                180                 185                 190

Glu Phe Pro Glu Tyr His Phe Ile His His Arg Leu Glu Lys Thr Tyr
            195                 200                 205

Val Glu Glu Gly Ser Phe Val Glu Gln His Glu Thr Ala Ile Ala Gln
            210                 215                 220

Leu Thr Thr Ile Gly Lys Pro Leu Gly Ser Leu His Glu Trp
225                 230                 235
```

What is claimed is:

1. An isolated and purified DNA encoding a humanized green fluorescent protein from *Ptilosarcus gurneyi* having the coding sequence of SEQ ID NO: 1.

2. An isolated and purified synthetic DNA encoding the green fluorescent protein of claim 1 having about at least 76% identity with the DNA sequence encoding wild type green fluorescent protein from *Ptilosarcus gurneyi*.

3. An isolated and purified synthetic DNA as in claim 1 wherein the codon usage is optimized for mammalian expression systems.

4. An isolated and purified synthetic DNA as in claim 2 wherein the codon usage is optimized for mammalian expression systems.

* * * * *